(12) United States Patent
Bateman et al.

(10) Patent No.: US 9,281,172 B2
(45) Date of Patent: Mar. 8, 2016

(54) CLOSED LOOP ION GUIDE WITH PSEUDO-POTENTIAL WELL

(75) Inventors: Robert Harold Bateman, Cheshire (GB); Kevin Giles, Cheshire (GB); Steven Derek Pringle, Darwen (GB); Jason Lee Wildgoose, Stockport (GB)

(73) Assignee: Micromass UK Limited, Wilmslow (GB)

(*) Notice: Subject to any disclaimer, the term of this patent is extended or adjusted under 35 U.S.C. 154(b) by 2031 days.

(21) Appl. No.: 12/094,561

(22) PCT Filed: Dec. 7, 2006

(86) PCT No.: PCT/GB2006/004574
§ 371 (c)(1),
(2), (4) Date: Aug. 20, 2008

(87) PCT Pub. No.: WO2007/066114
PCT Pub. Date: Jun. 14, 2007

(65) Prior Publication Data
US 2009/0014641 A1    Jan. 15, 2009

Related U.S. Application Data

(60) Provisional application No. 60/753,079, filed on Dec. 22, 2005.

(30) Foreign Application Priority Data

Dec. 7, 2005  (GB) .................................. 0524972.7

(51) Int. Cl.
H01J 49/36 (2006.01)
H01J 49/06 (2006.01)
G01N 27/62 (2006.01)

(52) U.S. Cl.
CPC ............ *H01J 49/062* (2013.01); *G01N 27/622* (2013.01)

(58) Field of Classification Search
CPC ..... H01J 49/0031; H01J 49/062; H01J 49/36; H01J 49/42; H01J 49/427; H01J 49/4275; H01J 49/429
USPC .................. 250/291, 281, 282, 287, 296, 297
See application file for complete search history.

(56) References Cited

U.S. PATENT DOCUMENTS

| | | | |
|---|---|---|---|
| 6,576,897 B1 | 6/2003 | Steiner et al. | |
| 6,791,078 B2 | 9/2004 | Giles et al. | |
| 6,891,157 B2 | 5/2005 | Bateman et al. | |
| 7,309,861 B2 | 12/2007 | Brown et al. | |
| 2002/0070339 A1* | 6/2002 | Clemmer ...................... 250/299 | |
| 2004/0026611 A1* | 2/2004 | Bateman et al. ............... 250/281 | |
| 2004/0031920 A1* | 2/2004 | Giles et al. ..................... 250/287 | |

(Continued)

FOREIGN PATENT DOCUMENTS

| | | |
|---|---|---|
| EP | 2403063 | 12/2004 |
| JP | H9(1997)213498 | 8/1997 |

(Continued)

*Primary Examiner* — B. Purinton
(74) *Attorney, Agent, or Firm* — Diederiks & Whitelaw, PLC

(57) ABSTRACT

A closed-loop ion guide is disclosed comprising a plurality of electrodes having apertures through which ions are transmitted in use. Ions are injected into the closed-loop ion guide and may make several circuits of the closed-loop ion guide before being ejected from the ion guide. In a mode of operation the ion guide may be arranged to separate ions temporally according to their ion mobility.

15 Claims, 11 Drawing Sheets

(56) References Cited

U.S. PATENT DOCUMENTS

2005/0151076 A1 7/2005 Yamaguchi et al.
2005/0199796 A1* 9/2005 Currell .................... 250/281

FOREIGN PATENT DOCUMENTS

| | | |
|---|---|---|
| JP | H09213498 | 8/1997 |
| JP | 2001143654 | 5/2001 |
| JP | 2001143655 | 5/2001 |
| JP | 2002110081 | 4/2002 |
| JP | 2005116246 | 4/2004 |
| JP | 2004158360 | 6/2004 |
| JP | 2004281350 | 10/2004 |
| WO | 2004/114347 | 12/2004 |

* cited by examiner

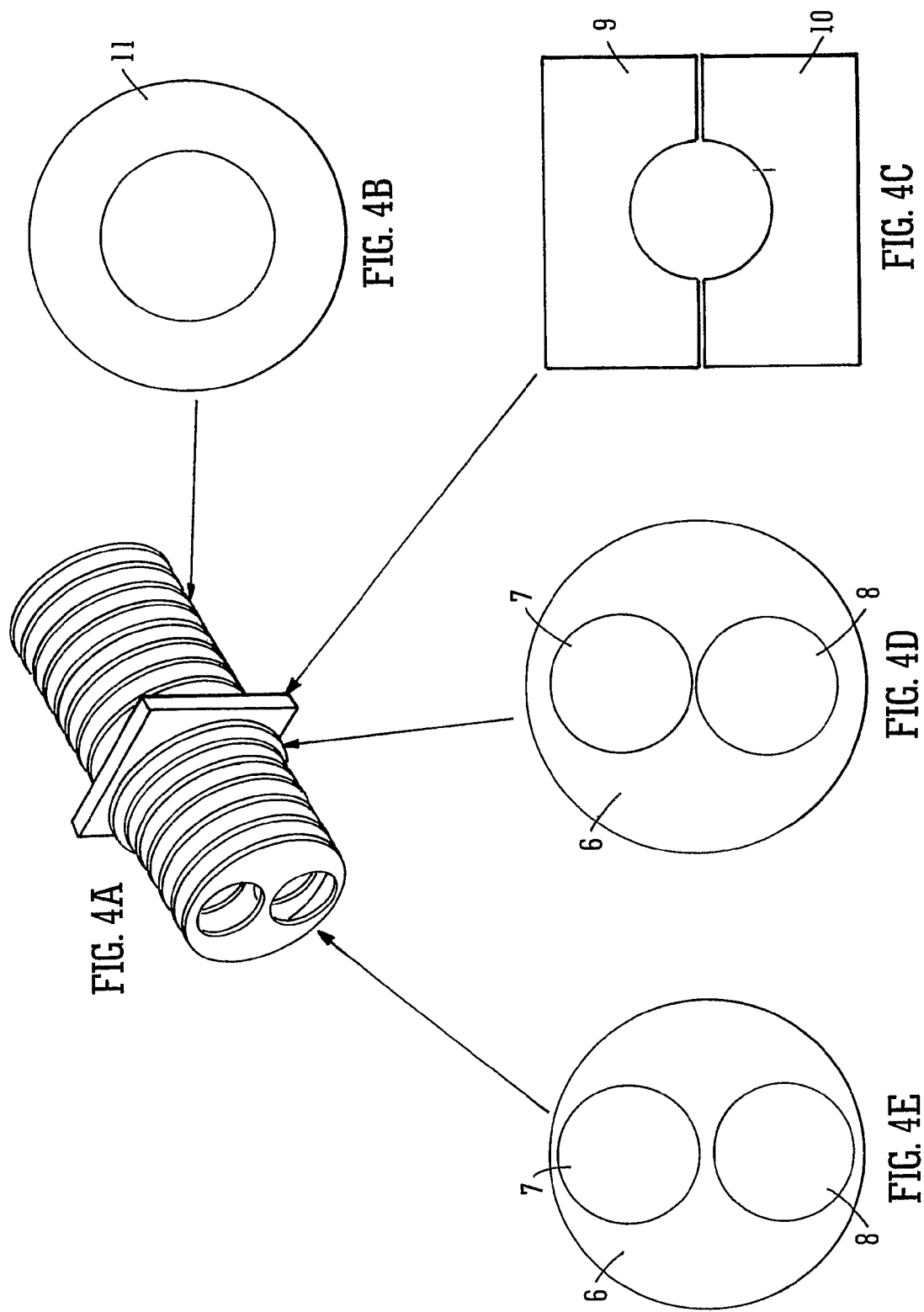

CLOSED LOOP ION GUIDE WITH PSEUDO-POTENTIAL WELL

CROSS REFERENCE TO RELATED APPLICATIONS

This application is the National Stage of International Application No. PCT/GB2006/004574, filed on Dec. 7, 2006, which claims priority to and benefit of U.S. Provisional Patent Application Ser. No. 60/753,079, filed on Dec. 22, 2005, and priority to and benefit of United Kingdom Patent Application No. 0524972.7, filed 7 Dec., 2005. The entire contents of these applications are incorporated herein by reference.

BACKGROUND OF THE INVENTION

The present invention relates to a mass spectrometer and a method of mass spectrometry.

Mass spectrometry is an established technique for identifying and quantifying molecules including molecules of biological interest. It is the primary technique for identifying proteins due to its unparalleled speed, sensitivity and specificity. Strategies for the analysis of proteins can involve either analysis of the intact protein or more commonly digestion of the protein using a specific protease that cleaves at predictable residues along the peptide backbone. This provides smaller stretches of peptide sequence that are more amenable to analysis via mass spectrometry.

These experiments typically involve separation of the complex digest mixture by liquid chromatography directly interfaced to a tandem mass spectrometer using Electrospray ionisation ("ESI"). MS and MS/MS spectra are collected throughout the chromatographic separation and this information can be used directly to search databases for matching sequences leading to identification of the parent protein.

This approach can be used to identify proteins that are present at low endogenous concentrations. However, such digest mixtures may contain many hundreds if not thousands of components, many of which will co-elute from the chromatography column. Methods designed for analysis of digest mixtures aim to identify as many of the peaks as possible within the complex mixture. As sample complexity increases it becomes increasingly difficult to select each individual precursor ion for subsequent fragmentation. One method to increase the peak capacity is a method known as "Shotgun" wherein a large number of parent or precursor ions are fragmented simultaneously and their fragment or daughter ions are recorded. Fragment or daughter ions are then associated with parent or precursor ions according to the closeness of alignment of their LC elution times. Eventually, as the sample complexity increases, even this method which represents an important advance in the art may sometimes fail.

Another method of dealing with the problem of highly complex mixtures is to further improve the separation capability. Addition of a further orthogonal separation stage can be particularly effective, especially if the time requirements for each separation process and for the mass spectrometry do not overlap.

One known method, which may be used to separate ions prior to analysis by mass spectrometry, is that of ion mobility spectrometry or gas phase electrophoresis. An ion mobility spectrometer is known comprising a drift tube or cell wherein an axial electric field is maintained along the length of the drift tube. A buffer gas is provided within the ion mobility spectrometer. Ions having a relatively high ion mobility pass relatively quickly along the ion mobility spectrometer whereas ions having a relatively low ion mobility pass more slowly. Ions are therefore temporally separated according to their ion mobility.

The ion mobility spectrometer may operate at or around atmospheric pressure, or under a partial vacuum at a pressure down to as low as 0.01 mbar. An ion mobility spectrometer operating under a partial vacuum is known comprising a plurality of electrodes having apertures wherein a DC voltage gradient is maintained along the length of the ion mobility spectrometer and the electrodes are connected to an AC or RF voltage supply. The frequency of the AC or RF voltage may be in the range 0.1-3.0 MHz. This form of ion mobility spectrometer is advantageous in that the application of the AC or RF voltage to the electrodes results in radial confinement of ions passing through the ion mobility spectrometer. Radial confinement of the ions results in higher ion transmission compared with ion mobility spectrometers which do not confine ions radially.

Another form of ion mobility separator is known wherein ions are confined radially by an inhomogeneous RF field and wherein ions are propelled forwards by a potential hill or barrier that moves along the axis of the ion guide in the presence of a buffer gas. Appropriate selection of the amplitude and velocity of the travelling potential barrier, and the type and pressure of gas, allows ions to selectively slip over the potential barrier according to their ion mobility. This in turn allows ions of different mobility to be transported at different velocities and thereby become temporally separated.

The additional separation gained by the use of an ion mobility separation (IMS) device or a gas phase electrophoresis device is known to increase the peak capacity of mass spectrometers (MS). This benefit is gained irrespective of whether or not other separation techniques, such as liquid chromatography (LC), are also used. Furthermore, the benefit gained by the use of ion mobility separation is equally relevant to tandem mass spectrometers (MS/MS) in which ions may be first mass analysed, then induced to fragment (CID) and the resulting fragment ions mass analysed.

In an ion mobility separator comprising a drift tube with a linear axial voltage gradient the maximum resolving power of the ion mobility separator is expressed by the ratio ($t_d/\Delta t_d$), where $t_d$ is the drift time and $\Delta t_d$ is the width of the mobility peak at its half height. It is determined by the physical construction of the device and is given by the following relationship:

$$\frac{t_d}{\Delta t_d} = \left[\frac{LEze}{16k_B T \ln 2}\right]^{1/2}$$

wherein E is the axial electric field, L is the length of the drift tube and T is the buffer gas temperature. The terms z, e and $k_B$ are the number of charges on the ion, the charge of an electron and Boltzmann's constant respectively.

In practice, there is a maximum field strength E that can be applied before electrical breakdown occurs. Also, at very high field strengths the device begins to become non-linear. Therefore, typically the length of the drift tube is increased in order to increase the separator's resolution. As a consequence the voltage applied across the drift tube is increased. In addition, in a conventional drift tube the beam divergence increases with its length and therefore the drift tube diameter needs to increase with its length. Eventually the instrument dimensions become unacceptably large.

The problem of beam divergence may be overcome in a drift tube operating at low pressure (less than 100 mbar) by the use of inhomogeneous RF fields to confine ions in the radial direction. Furthermore, the difficulties resulting from the need to apply a large voltage across the length of a long drift tube may be overcome by use of a superimposed travelling wave on the drift tube. Here a relatively low voltage is adequate. However, the inconvenience resulting from the use of a very long drift tube remains.

This problem is compounded if it is required to separate ions according to their ion mobility with high resolution, then alter the ions in a particular way, and then further separate the resulting products according to their ion mobility, also with high resolution. For example, ions separated according to their ion mobility may subsequently be partially unfolded, fully unfolded or fragmented by energetic collisions with gas molecules. Hence, an experiment may require a long drift tube to separate ions according to their ion mobility, a collision region in which to induce unfolding or fragmentation of the ions, and then a second long drift tube to separate product ions according to their ion mobility. In each case the ion mobility separation may be required with high resolution. A mass spectrometer having two long drift tubes will, however, be unacceptably long.

It is possible to envisage more complex experiments which would require even more stages. For example, an even more complex experiment may entail separation of ions by a first IMS stage, collisionally induced unfolding, separation of unfolded ions by a second IMS stage, collisionally induced fragmentation, separation of product ions by a third IMS stage, and finally mass analysis by mass spectrometry.

Equipment designed to carry out specific experiments will also be inflexible. For example, equipment designed to carry out only simple experiments will not be capable of carrying out more complex experiments. Conversely, equipment designed to carry out complex experiments may not be able to carry out simple experiments without some compromise in performance.

It is therefore desired to provide an improved mass spectrometer.

SUMMARY OF THE INVENTION

According to an aspect of the present invention there is provided a mass spectrometer comprising a closed-loop ion guide comprising a plurality of electrodes.

In a mode of operation ions are preferably arranged to make multiple circuits or rotations of or around the closed-loop ion guide. In a mode of operation at least 50%, 60%, 70%, 80%, 90%, 95% or 100% of the ions within the closed-loop ion guide may be arranged to move in substantially the same direction or rotate in substantially the same sense along or around the closed-loop ion guide at a particular moment in time.

A non-zero DC voltage gradient is preferably maintained across one or more sections or portions of the ion guide. The integral of the axial DC voltage gradient around the closed-loop ion guide is preferably substantially zero.

The ion guide preferably comprises a curved, labyrinthine, tortuous, serpentine or circuitous ion guiding path which forms a circuit or circular path or convoluted path. Ions preferably rotate or change direction as they are moved around the closed-loop ion guide.

In a mode of operation ions are preferably arranged to rotate or circulate around the closed-loop ion guide. In a mode of operation ions are preferably arranged to make at least one, two, three, four, five, six, seven, eight, nine, ten or more than ten circuits of the ion guide.

According to a particularly preferred embodiment the plurality of electrodes preferably comprise electrodes having apertures through which ions are transmitted in use. Preferably, at least 1%, 5%, 10%, 20%, 30%, 40%, 50%, 60%, 70%, 80%, 90%, 95% or 100% of the electrodes have substantially circular, rectangular, square or elliptical apertures.

According to the preferred embodiment at least 1%, 5%, 10%, 20%, 30%, 40%, 50%, 60%, 70%, 80%, 90%, 95% or 100% of the electrodes have apertures which are substantially the same size or which have substantially the same area. According to other embodiments at least 1%, 5%, 10%, 20%, 30%, 40%, 50%, 60%, 70%, 80%, 90%, 95% or 100% of the electrodes have apertures which become progressively larger and/or smaller in size or in area in a direction along the axis or length of the ion guide.

At least 1%, 5%, 10%, 20%, 30%, 40%, 50%, 60%, 70%, 80%, 90%, 95% or 100% of the electrodes preferably have apertures having internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm. According to the preferred embodiment at least 1%, 5%, 10%, 20%, 30%, 40%, 50%, 60%, 70%, 80%, 90%, 95% or 100% of the electrodes are spaced apart from one another by an axial distance selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

At least some of the plurality of electrodes preferably comprise apertures, wherein the ratio of the internal diameter or dimension of the apertures to the centre-to-centre axial spacing between adjacent electrodes is selected from the group consisting of: (i) <1.0; (ii) 1.0-1.2; (iii) 1.2-1.4; (iv) 1.4-1.6; (v) 1.6-1.8; (vi) 1.8-2.0; (vii) 2.0-2.2; (viii) 2.2-2.4; (ix) 2.4-2.6; (x) 2.6-2.8; (xi) 2.8-3.0; (xii) 3.0-3.2; (xiii) 3.2-3.4; (xiv) 3.4-3.6; (xv) 3.6-3.8; (xvi) 3.8-4.0; (xvii) 4.0-4.2; (xviii) 4.2-4.4; (xix) 4.4-4.6; (xx) 4.6-4.8; (xxi) 4.8-5.0; and (xxii) >5.0.

According to an embodiment at least 1%, 5%, 10%, 20%, 30%, 40%, 50%, 60%, 70%, 80%, 90%, 95% or 100% of the electrodes have a thickness or axial length selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

According to a less preferred embodiment the ion guide may comprise a segmented rod set ion guide. The ion guide may, for example, comprise a segmented quadrupole, hexapole or octapole ion guide or an ion guide comprising more than eight segmented rod sets. According to an embodiment the ion guide may comprise a plurality of electrodes having a cross-section selected from the group consisting of: (i) an approximately or substantially circular cross-section; (ii) an approximately or substantially hyperbolic surface; (iii) an arcuate or part-circular cross-section; (iv) an approximately or substantially rectangular cross-section; and (v) an approximately or substantially square cross-section.

According to another embodiment the ion guide may comprise a plurality of plate electrodes, wherein a plurality of groups of electrodes are arranged along the axial length of the ion guide. Each group of electrodes preferably comprises a first electrode and a second electrode. The first and second electrodes are preferably arranged substantially in the same plane and are preferably arranged either side of the central longitudinal axis of the ion guide. The mass spectrometer preferably further comprises means for applying a DC voltage or potential to the first and second electrodes in order to confine ions in a first radial direction within the ion guide. Each group of electrodes preferably further comprises a third electrode and a fourth electrode. The third and fourth electrodes are preferably arranged substantially in the same plane as the first and second electrodes and are arranged either side of the central longitudinal axis of the ion guide in a different orientation to the first and second electrodes. The means for applying an AC or RF voltage is preferably arranged to apply the AC or RF voltage to the third and fourth electrodes in order to confine ions in a second radial direction (which is preferably orthogonal to the first radial direction) within the ion guide.

According to another embodiment the ion guide may comprise a stack or array of planar, plate or mesh electrodes. The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes. Preferably, at least 1%, 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use.

According to a further embodiment the ion guide may comprise one or more rod set electrodes and a plurality of ring electrodes arranged around the one or more rod set electrodes.

The mass spectrometer preferably further comprises AC or RF voltage means for supplying an AC or RF voltage to the electrodes comprising the closed-loop ion guide. The AC or RF voltage preferably generates a pseudo-potential well which acts to confine ions radially within the closed-loop ion guide. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xiii) 9.0-9.5 MHz; (xxiv) 9.5-10.0 MHz; and (xxv) >10.0 MHz.

The ion guide preferably comprises n axial segments, wherein n is selected from the group consisting of: (i) 1-10; (ii) 11-20; (iii) 21-30; (iv) 31-40; (v) 41-50; (vi) 51-60; (vii) 61-70; (viii) 71-80; (ix) 81-90; (x) 91-100; and (xi) >100. Each axial segment preferably comprises 1, 2, 3, 4, 5, 6, 7, 8, 9, 10, 11, 12, 13, 14, 15, 16, 17, 18, 19, 20 or >20 electrodes.

The axial length of at least 1%, 5%, 10%, 20%, 30%, 40%, 50%, 60%, 70%, 80%, 90%, 95% or 100% of the axial segments is preferably selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm. The spacing between at least 1%, 5%, 10%, 20%, 30%, 40%, 50%, 60%, 70%, 80%, 90%, 95% or 100% of the axial segments is preferably selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

The ion guide preferably has a length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; and (xi) >200 mm. The ion guide preferably comprises at least: (i) 10-20 electrodes; (ii) 20-30 electrodes; (iii) 30-40 electrodes; (iv) 40-50 electrodes; (v) 50-60 electrodes; (vi) 60-70 electrodes; (vii) 70-80 electrodes; (viii) 80-90 electrodes; (ix) 90-100 electrodes; (x) 100-110 electrodes; (xi) 110-120 electrodes; (xii) 120-130 electrodes; (xiii) 130-140 electrodes; (xiv) 140-150 electrodes; or (xv) >150 electrodes.

According to a particularly preferred embodiment the mass spectrometer preferably further comprises means for driving or urging ions along or around at least 1%, 5%, 10%, 20%, 30%, 40%, 50%, 60%, 70%, 80%, 90%, 95% or 100% of the length or ion guiding path of the ion guide.

The means for driving or urging ions preferably comprises means for applying one more transient DC voltages or potentials or DC voltage or potential waveforms to at least 1%, 5%, 10%, 20%, 30%, 40%, 50%, 60%, 70%, 80%, 90%, 95% or 100% of the electrodes. The one or more transient DC voltages or potentials or DC voltage or potential waveforms preferably create: (i) a potential hill or barrier; (ii) a potential well; (iii) multiple potential hills or barriers; (iv) multiple potential wells; (v) a combination of a potential hill or barrier and a potential well; or (vi) a combination of multiple potential hills or barriers and multiple potential wells.

The one or more transient DC voltage or potential waveforms preferably comprise a repeating waveform or square wave. In use a plurality of axial DC potential wells may be translated along the length of the ion guide or a plurality of transient DC potentials or voltages may be progressively applied to electrodes along the axial length of the ion guide.

According to an embodiment the mass spectrometer preferably comprises first means arranged and adapted to progressively increase, progressively decrease, progressively vary, scan, linearly increase, linearly decrease, increase in a stepped, progressive or other manner or decrease in a stepped, progressive or other manner the amplitude, height or depth of the one or more transient DC voltages or potentials or DC voltage or potential waveforms by $x_1$ Volts over a time period $t_1$. Preferably, $x_1$ is selected from the group consisting of: (i) <0.1 V; (ii) 0.1-0.2 V; (iii) 0.2-0.3 V; (iv) 0.3-0.4 V; (v) 0.4-0.5 V; (vi) 0.5-0.6 V; (vii) 0.6-0.7 V; (viii) 0.7-0.8 V; (ix) 0.8-0.9 V; (x) 0.9-1.0 V; (xi) 1.0-1.5 V; (xii) 1.5-2.0 V; (xiii) 2.0-2.5 V; (xiv) 2.5-3.0 V; (xv) 3.0-3.5 V; (xvi) 3.5-4.0 V; (xvii) 4.0-4.5 V; (xviii) 4.5-5.0 V; (xix) 5.0-5.5 V; (xx) 5.5-6.0 V; (xxi) 6.0-6.5 V; (xxii) 6.5-7.0 V; (xxiii) 7.0-7.5 V; (xxiv) 7.5-8.0 V; (xxv) 8.0-8.5 V; (xxvi) 8.5-9.0 V; (xxvii) 9.0-9.5 V; (xxviii) 9.5-10.0 V; and (xxix) >10.0 V. Preferably, $t_1$ is selected from the group consisting of: (i) <1 ms; (ii) 1-10 ms; (iii) 10-20 ms; (iv) 20-30 ms; (v) 30-40 ms; (vi) 40-50 ms; (vii) 50-60 ms; (viii) 60-70 ms; (ix) 70-80 ms; (x) 80-90 ms; (xi) 90-100 ms; (xii) 100-200 ms; (xiii) 200-300 ms; (xiv) 300-400 ms; (xv) 400-500 ms; (xvi) 500-600 ms; (xvii) 600-

700 ms; (xviii) 700-800 ms; (xix) 800-900 ms; (xx) 900-1000 ms; (xxi) 1-2 s; (xxii) 2-3 s; (xxiii) 3-4 s; (xxiv) 4-5 s; and (xxv) >5 s.

According to an embodiment the mass spectrometer preferably further comprises second means arranged and adapted to progressively increase, progressively decrease, progressively vary, scan, linearly increase, linearly decrease, increase in a stepped, progressive or other manner or decrease in a stepped, progressive or other manner the velocity or rate at which the one or more transient DC voltages or potentials or DC voltage or potential waveforms are applied to the electrodes by $x_2$ m/s over a time period $t_2$. Preferably, $x_2$ is selected from the group consisting of: (i) <1; (ii) 1-2; (iii) 2-3; (iv) 3-4; (v) 4-5; (vi) 5-6; (vii) 6-7; (viii) 7-8; (ix) 8-9; (x) 9-10; (xi) 10-11; (xii) 11-12; (xiii) 12-13; (xiv) 13-14; (xv) 14-15; (xvi) 15-16; (xvii) 16-17; (xviii) 17-18; (xix) 18-19; (xx) 19-20; (xxi) 20-30; (xxii) 30-40; (xxiii) 40-50; (xxiv) 50-60; (xxv) 60-70; (xxvi) 70-80; (xxvii) 80-90; (xxviii) 90-100; (xxix) 100-150; (xxx) 150-200; (xxxi) 200-250; (xxxii) 250-300; (xxxiii) 300-350; (xxxiv) 350-400; (xxxv) 400-450; (xxxvi) 450-500; and (xxxvii) >500. Preferably, $t_2$ is selected from the group consisting of: (i) <1 ms; (ii) 1-10 ms; (iii) 10-20 ms; (iv) 20-30 ms; (v) 30-40 ms; (vi) 40-50 ms; (vii) 50-60 ms; (viii) 60-70 ms; (ix) 70-80 ms; (x) 80-90 ms; (xi) 90-100 ms; (xii) 100-200 ms; (xiii) 200-300 ms; (xiv) 300-400 ms; (xv) 400-500 ms; (xvi) 500-600 ms; (xvii) 600-700 ms; (xviii) 700-800 ms; (xix) 800-900 ms; (xx) 900-1000 ms; (xxi) 1-2 s; (xxii) 2-3 s; (xxiii) 3-4 s; (xxiv) 4-5 s; and (xxv) >5 s.

According to an embodiment the mass spectrometer comprises means arranged to maintain a constant non-zero DC voltage gradient along at least 1%, 5%, 10%, 20%, 30%, 40%, 50%, 60%, 70%, 80%, 90%, 95% or 100% of the length or ion guiding path of the ion guide.

According to a particularly preferred embodiment one or more portions of the ion guide may comprise an ion mobility spectrometer or separator portion, section or stage. Ions are preferably caused to separate temporally according to their ion mobility in the ion mobility spectrometer or separator portion, section or stage.

According to another embodiment one or more portions of the ion guide may comprise a Field Asymmetric Ion Mobility Spectrometer ("FAIMS") portion, section or stage wherein ions are caused to separate temporally according to their rate of change of ion mobility with electric field strength in the Field Asymmetric Ion Mobility Spectrometer ("FAIMS") portion, section or stage.

According to the preferred embodiment a buffer gas is preferably provided in use within one or more sections of the ion guide. In a mode of operation ions are preferably arranged to be collisionally cooled without fragmenting upon interaction with gas molecules within a portion or region of the ion guide.

In a mode of operation ions are preferably arranged to be heated upon interaction with gas molecules within a portion or region of the ion guide.

In a mode of operation ions are preferably arranged to be fragmented upon interaction with gas molecules within a portion or region of the ion guide.

In a mode of operation ions are preferably arranged to unfold or at least partially unfold upon interaction with gas molecules within a portion or region of the ion guide.

In a mode of operation ions are preferably trapped axially within a portion or region of the ion guide.

The mass spectrometer preferably comprises means for injecting ions into the ion guide. The means for injecting ions may comprise one, two, three or more than three discrete ion guiding channels or input ion guiding regions through which ions may preferably be injected into the ion guide. The means for injecting ions may comprise a plurality of electrodes, each electrode preferably comprising one, two, three or more than three apertures. The means for injecting ions may comprise one or more deflection electrodes. One or more voltages are preferably applied to the one or more deflection electrodes in order to direct ions from one or more ion guiding channels or input ion guiding regions into the ion guide.

According to an embodiment the mass spectrometer preferably further comprises means for ejecting ions from the ion guide. The means for ejecting ions preferably comprises one, two, three or more than three discrete ion guiding channels or exit ion guiding regions into which ions may be ejected from the ion guide. The means for ejecting ions may comprise a plurality of electrodes, each electrode comprising one, two, three or more than three apertures. According to an embodiment the means for ejecting ions preferably further comprises one or more deflection electrodes. One or more voltages are preferably applied to the one or more deflection electrodes in order to direct ions from the ion guide into one or more ion guiding channels or exit ion guiding regions.

The mass spectrometer preferably comprises means for maintaining in a mode of operation at least a portion of the ion guide at a pressure selected from the group consisting of: (i) $>1.0\times10^{-3}$ mbar; (ii) $>1.0\times10^{-2}$ mbar; (iii) $>1.0\times10^{-1}$ mbar; (iv) $>1$ mbar; (v) $>10$ mbar; (vi) $>100$ mbar; (vii) $>5.0\times10^{-3}$ mbar; (viii) $>5.0\times10^{-2}$ mbar; (ix) $10^{-4}$-$10^{-3}$ mbar; (x) $10^{-3}$-$10^{-2}$ mbar; and (xi) $10^{-2}$-$10^{-1}$ mbar.

The mass spectrometer preferably comprises means for maintaining in a mode of operation at least a length L of the ion guide at a pressure P wherein the product P×L is selected from the group consisting of: (i) $\geq 1.0\times10^{-3}$ mbar cm; (ii) $\geq 1.0\times10^{-2}$ mbar cm; (iii) $\geq 1.0\times10^{-1}$ mbar cm; (iv) $\geq 1$ mbar cm; (v) $\geq 10$ mbar cm; (vi) $\geq 10^2$ mbar cm; (vii) $\geq 10^3$ mbar cm; (viii) $\geq 10^4$ mbar cm; and (ix) $\geq 10^5$ mbar cm.

According to the preferred embodiment the mass spectrometer preferably further comprises an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source. The ion source may comprise a continuous or pulsed ion source.

The mass spectrometer may further comprise one or more mass filters arranged upstream of and/or within and/or downstream of the closed-loop ion guide. The one or more mass filters may be selected from the group consisting of: (i) a quadrupole rod set mass filter; (ii) a Time of Flight mass filter or mass spectrometer; (iii) a Wein filter; and (iv) a magnetic sector mass filter or mass spectrometer. According to a particularly preferred embodiment one or more mass filters may form part of the closed-loop ion guide.

According to an embodiment the mass spectrometer may comprise one or more further ion guides or ion traps arranged upstream of and/or within and/or downstream of the closed-loop ion guide. The one or more further ion guides or ion traps may be selected from the group consisting of:

(i) a multipole rod set or a segmented multipole rod set ion guide or ion trap comprising a quadrupole rod set, a hexapole rod set, an octapole rod set or a rod set comprising more than eight rods;

(ii) an ion tunnel or ion funnel ion guide or ion trap comprising a plurality of electrodes or at least 2, 5, 10, 20, 30, 40, 50, 60, 70, 80, 90 or 100 electrodes having apertures through which ions are transmitted in use, wherein at least 1%, 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area;

(iii) a stack or array of planar, plate or mesh electrodes, wherein the stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes or at least 1%, 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use; and (iv) an ion trap or ion guide comprising a plurality of groups of electrodes arranged axially along the length of the ion trap or ion guide, wherein each group of electrodes comprises: (a) a first and a second electrode and means for applying a DC voltage or potential to the first and second electrodes in order to confine ions in a first radial direction within the ion guide; and (b) a third and a fourth electrode and means for applying an AC or RF voltage to the third and fourth electrodes in order to confine ions in a second radial direction within the ion guide.

The one or more further ion guides or ion traps preferably comprise an ion tunnel or ion funnel ion guide or ion trap wherein at least 1%, 5%, 10%, 15%, 20%, 25%, 30%, 35%, 40%, 45%, 50%, 55%, 60%, 65%, 70%, 75%, 80%, 85%, 90%, 95% or 100% of the electrodes preferably have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The one or more further ion guides or ion traps preferably further comprise second AC or RF voltage means arranged and adapted to apply an AC or RF voltage to at least 1%, 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the one or more further ion guides or ion traps in order to confine ions radially within the one or more further ion guides or ion traps.

The one or more further ion guides or ion traps are preferably arranged and adapted to receive a beam or group of ions and to convert or partition the beam or group of ions such that at least 1, 2, 3, 4, 5, 6, 7, 8, 9, 10, 11, 12, 13, 14, 15, 16, 17, 18, 19 or 20 separate packets of ions are confined and/or isolated within the one or more further ion guides or ion traps at any particular time. Each packet of ions is preferably separately confined and/or isolated in a separate axial potential well formed in the one or more further ion guides or ion traps.

The mass spectrometer may comprise means arranged and adapted to urge at least some ions upstream and/or downstream through or along at least 1%, 5%, 10%, 15%, 20%, 25%, 30%, 35%, 40%, 45%, 50%, 55%, 60%, 65%, 70%, 75%, 80%, 85%, 90%, 95% or 100% of the axial length of the one or more further ion guides or ion traps in a mode of operation.

The mass spectrometer may comprise transient DC voltage means arranged and adapted to apply one or more transient DC voltages or potentials or one or more transient DC voltage or potential waveforms to the electrodes forming the one or more further ion guides or ion traps in order to urge at least some ions downstream and/or upstream along at least 1%, 5%, 10%, 15%, 20%, 25%, 30%, 35%, 40%, 45%, 50%, 55%, 60%, 65%, 70%, 75%, 80%, 85%, 90%, 95% or 100% of the axial length of the one or more further ion guides or ion traps.

The mass spectrometer may comprise AC or RF voltage means arranged and adapted to apply two or more phase-shifted AC or RF voltages to electrodes forming the one or more further ion guides or ion traps in order to urge at least some ions downstream and/or upstream along at least 1%, 5%, 10%, 15%, 20%, 25%, 30%, 35%, 40%, 45%, 50%, 55%, 60%, 65%, 70%, 75%, 80%, 85%, 90%, 95% or 100% of the axial length of the one or more further ion guides or ion traps.

According to an embodiment the mass spectrometer further comprises means arranged and adapted to maintain at least a portion of the one or more further ion guides or ion traps at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >1 mbar; (viii) 0.0001-100 mbar; and (ix) 0.001-10 mbar.

A collision, fragmentation or reaction device may be provided upstream of and/or within and/or downstream of the closed-loop ion guide. The collision, fragmentation or reaction device is preferably arranged and adapted to fragment ions by Collision Induced Dissociation ("CID"). However, according to other embodiments the collision, fragmentation or reaction device may be selected from the group consisting of: (i) a Surface Induced Dissociation ("SID") fragmentation device; (ii) an Electron Transfer Dissociation ("ETD") fragmentation device; (iii) an Electron Capture Dissociation ("ECD") fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultra-violet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The mass spectrometer preferably further comprises a mass analyser arranged upstream of and/or within and/or downstream of the closed-loop ion guide. The mass analyser is preferably selected from the group consisting of: (i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass analyser; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap; (xii) an electrostatic Ion Cyclotron Resonance mass analyser; (xiii) an electrostatic Fourier Transform mass analyser; and (xiv) a quadrupole rod set mass filter or mass analyser.

According to another aspect of the present invention there is provided a method of mass spectrometry comprising:

guiding ions through a closed-loop ion guide comprising a plurality of electrodes.

According to another aspect of the present invention there is provided a mass spectrometer comprising a closed-loop ion guide comprising a mass filter and a collision, fragmentation or reaction device wherein in a mode of operation fragment or daughter ions produced in the collision, fragmentation or reaction device pass via the closed-loop ion guide to the mass filter.

According to another aspect of the present invention there is provided a method of mass spectrometry comprising:

providing a closed-loop ion guide comprising a mass filter and a collision, fragmentation or reaction device; and passing fragment or daughter ions produced in the collision, fragmentation or reaction device via the closed-loop ion guide to the mass filter.

According to another aspect of the present invention there is provided a mass spectrometer comprising:

a closed-loop ion guide comprising a plurality of electrodes;

means for maintaining in a mode of operation at least a length L of the ion guide at a pressure P wherein the product P×L is selected from the group consisting of: (i) $\geq 1.0 \times 10^{-3}$ mbar cm; (ii) $\geq 1.0 \times 10^{-2}$ mbar cm; (iii) $\geq 1.0 \times 10^{-1}$ mbar cm; (iv) $\geq 1$ mbar cm; (v) $\geq 10$ mbar cm; (vi) $\geq 10^2$ mbar cm; (vii) $\geq 10^3$ mbar cm; (viii) $\geq 10^4$ mbar cm; and (ix) $\geq 10^5$ mbar cm;

AC or RF voltage means for supplying an AC or RF voltage to the electrodes, the AC or RF voltage generating in use a pseudo-potential well which acts to confine ions radially within the closed-loop ion guide;

means arranged to maintain a constant non-zero DC voltage gradient along at least 1%, 5%, 10%, 20%, 30%, 40%, 50%, 60%, 70%, 80%, 90%, 95% or 100% of the length or ion guiding path of the ion guide; and means for applying one more transient DC voltages or potentials or DC voltage or potential waveforms to at least 1%, 5%, 10%, 20%, 30%, 40%, 50%, 60%, 70%, 80%, 90%, 95% or 100% of the electrodes.

The ion guide preferably comprises either an ion mobility spectrometer or separator, or a collision, fragmentation or reaction device.

According to another aspect of the present invention there is provided a method of mass spectrometry comprising:

providing a closed-loop ion guide comprising a plurality of electrodes;

maintaining in a mode of operation at least a length L of the ion guide at a pressure P wherein the product P×L is selected from the group consisting of: (i) $\geq 1.0 \times 10^{-3}$ mbar cm; (ii) $\geq 1.0 \times 10^{-2}$ mbar cm; (iii) $\geq 1.0 \times 10^{-1}$ mbar cm; (iv) $\geq 1$ mbar cm; (v) $\geq 10$ mbar cm; (vi) $\geq 10^2$ mbar cm; (vii) $\geq 10^3$ mbar cm; (viii) $\geq 10^4$ mbar cm; and (ix) $\geq 10^5$ mbar cm;

supplying an AC or RF voltage to the electrodes, the AC or RF voltage generating a pseudo-potential well which acts to confine ions radially within the closed-loop ion guide;

maintaining a constant non-zero DC voltage gradient along at least 1%, 5%, 10%, 20%, 30%, 40%, 50%, 60%, 70%, 80%, 90%, 95% or 100% of the length or ion guiding path of the ion guide; and applying one more transient DC voltages or potentials or DC voltage or potential waveforms to at least 1%, 5%, 10%, 20%, 30%, 40%, 50%, 60%, 70%, 80%, 90%, 95% or 100% of the electrodes in order to drive or urge ions.

Conventional 2D linear ion traps and 3D quadrupole ion traps should not be construed as comprising a closed-loop ion guide within the meaning of the present invention. In conventional ion traps, ions do not follow a circuitous ion guiding path within the meaning of the preferred embodiment.

A mass spectrometer according to the preferred embodiment is capable of high resolution ion mobility separation and is also preferably capable of carrying out both simple and complex experiments, without compromise in performance and without being excessively large.

The preferred embodiment relates to one or more ion guides arranged so as to form a closed-loop. A buffer gas is introduced into or is present within the closed-loop ion guide. One or more transient DC potentials or voltages or one or more transient DC potential or voltage waveforms are preferably applied to at least one section of the closed-loop ion guide. Ions are preferably propelled or urged by the one or more transient DC potentials or voltages or one or more transient DC potential or voltage waveforms, which are preferably applied to at least one section of the ion guide, through or around the closed-loop ion guide in a desired direction.

According to the preferred embodiment an RF voltage is applied to the electrodes comprising the one or more closed-loop ion guides in order to confine ions radially within the closed-loop ion guide about the central axis of the ion guide. Ions are preferably confined in a radial pseudo-potential well within the ion guide.

One or more of the ion guides may comprise a quadrupole rod set, a hexapole rod set, an octopole rod set, a segmented multi-pole rod set, a stacked ring set, an ion tunnel, an ion funnel or a parallel plate assembly (sandwich plates) or other arrangement of electrodes to which RF voltages may be applied to give inhomogeneous RF electric fields.

According to the preferred embodiment one or more transient DC potentials or voltages or one or more transient DC potential or voltage waveforms are preferably applied to the electrodes of the preferred ion guide in order to propel or urge ions in the direction of travel of the one or more transient DC potentials or voltages or one or more transient DC potential or voltage waveforms.

A buffer gas is preferably provided within at least one of the ion guides so that collisions between ions and gas molecules occur frequently. Collisions with gas molecules may be used either to cool ions or to heat ions. Collisions between ions and gas molecules may impose a drag on the motion of the ions which may be exploited in order to separate ions according to their ion mobility.

Collision with gas molecules may be used to cool or thermalise ions so that their kinetic energies are reduced. This is particularly advantageous if ions are to be guided around corners as is necessary in a closed-loop arrangement. Low energy or thermalised ions will preferably collapse towards the central axis of the RF ion guide. In order to cool ions by collisions with gas molecules a pressure in excess of $10^{-4}$ mbar is preferably required, further preferably in excess of $10^{-3}$ mbar.

Collisions with gas molecules may additionally and/or alternatively be used to heat ions so that their internal energies are increased. This is required if ions are to be unfolded and/or fragmented.

Ions may be induced to fragment by first accelerating the ions to a relatively high kinetic energy, generally greater than 10 or 15 eV. The ions are then preferably collided into gas molecules. Alternatively, ions may be accelerated through a region with adequately high gas pressure or propelled by one or more transient DC potentials or voltages or one or more transient DC potential or voltage waveforms through a region with adequate gas pressure. Molecular ions propelled through a buffer gas at velocities in excess of about 500 to 1000 m/s will give rise to energetic ion-molecule collisions. Energetic ion-molecule collisions will preferably lead to increased internal energy of the ion and may lead to unfolding of the ion where appropriate. The ions may alternatively and/or additionally be caused to fragment. In order to heat and fragment ions by collisions with gas molecules a pressure in excess of $10^{-4}$ mbar is preferably required, further preferably in excess of $10^{-3}$ mbar.

If ion motion is impeded by the viscous drag of the buffer gas then ions may be separated according to their ion mobility. Ions having a relatively high ion mobility will travel faster than ions having a relatively low ion mobility for the same conditions of gas pressure and electric field strengths. This characteristic can be used to separate ions spatially and temporally. In order to separate ions according to their ion mobility a pressure in excess of $10^{-2}$ mbar is preferably provided, further preferably in excess of $10^{-1}$ mbar.

In a preferred embodiment the pressure in one or more of the preferred ion guides may be adequate to allow collision induced unfolding of ions and/or fragmentation of ions and/or separation of ions according to their ion mobility.

The presence of gas in one or more of the ion guides will preferably dampen the ion motion and cause ions to slow down and eventually lose all forward motion. It is therefore desirable to provide a means of driving ions forwards. In a preferred embodiment ions are preferably driven forwards by means of one or more transient DC potentials or voltages or one or more transient DC potential or voltage waveforms. One or more transient DC potentials or voltages or one or more transient DC potential or voltage waveforms may be used to drive ions around the closed-loop ion guide as many times as desired.

According to a less preferred embodiment ions may be driven forwards along or around a section of the closed-loop ion guide by a constant axial DC voltage gradient. However, it is not possible to impose a DC voltage gradient around a closed-loop without at some point having a voltage gradient which acts to oppose ion motion. One or more transient DC potentials or voltages or one or more transient DC potential or voltage waveforms may be superimposed to the electrodes of the closed-loop ion guide at this point in order to drive ions forward against the opposing DC axial electric field.

In a preferred embodiment ions may be introduced or switched into the closed-loop ion guide by one or more ion deflectors or diverters. Furthermore, in a preferred embodiment ions may be removed, switched or diverted out from the closed-loop ion guide by one or more deflectors or diverters.

BRIEF DESCRIPTION OF THE DRAWINGS

Various embodiments of the present invention will now be described, by way of example only, and with reference to the accompanying drawings in which:

FIGS. 4A-4E show a device for introducing or removing ions from a preferred closed-loop ion guide;

DETAILED DESCRIPTION OF THE PREFERRED EMBODIMENTS

Figure 1:
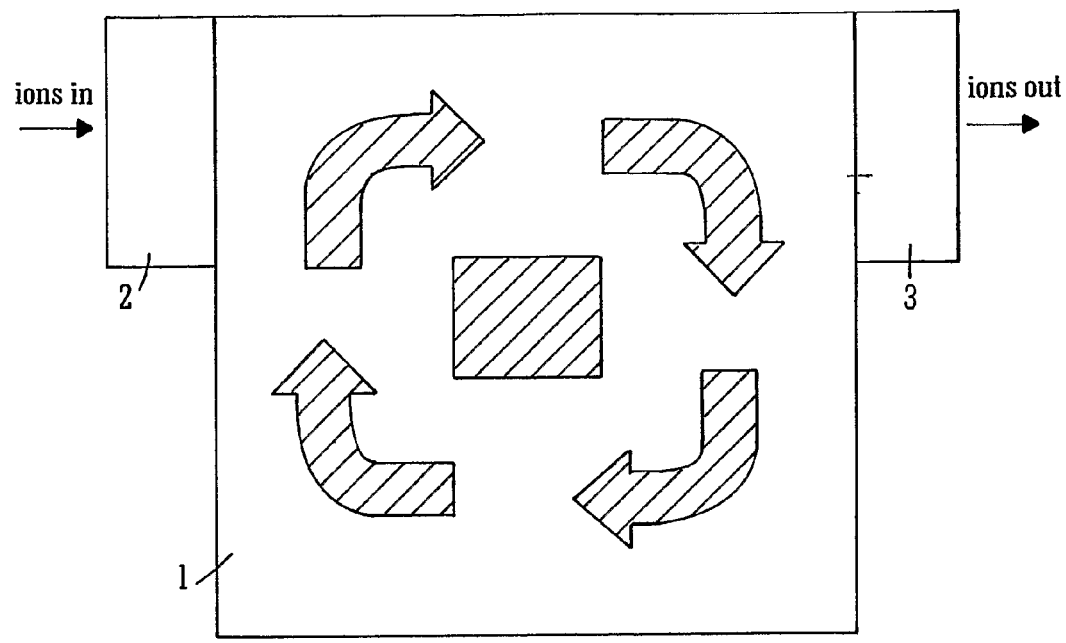
FIG. 1 shows a closed-loop ion guide according to a preferred embodiment of the present invention.

A preferred embodiment of the present invention will now be described with reference to FIG. 1. According to the preferred embodiment a mass spectrometer is provided comprising a closed-loop ion guide 1. Ions are preferably injected into the closed-loop ion guide 1 and the ions are preferably caused to make several rotations or circuits around the ion guide 1. Ions are then preferably ejected or removed from the ion guide 1. According to the preferred embodiment ions preferably pass a fixed point of the ion guide circuit a number of times as the ions circulate around the ion guide 1. The ions preferably make several circuits of the ion guide 1 in a mode of operation.

Ions within the ion guide 1 are preferably caused to move in substantially the same direction around the ion guide 1 at substantially the same time. Ions may, for example, make one, two, three, four, five, six, seven, eight, nine, ten or more than ten passes or circuits around the ion guide 1 before the ions are ejected from the ion guide 1.

The ion guide 1 preferably comprises a circular or curved ion guiding path. Embodiments are contemplated, however, wherein the ion guiding path may comprise one or more straight sections with curved interconnecting sections. The ion guiding path may be relatively complex. For example, the ion guiding path may be labyrinthine, tortuous or serpentine. In contrast to a 2D linear ion trap or a 3D ion trap, ions preferably make circuits around the closed-loop ion guide 1.

A buffer gas is preferably provided within at least a part or section of the closed-loop ion guide 1. In a mode of operation ions may be collisionally cooled or alternatively collisionally heated by interaction with the buffer gas. In a mode of operation ions may be accelerated such that ions are fragmented upon colliding with the gas molecules present within a portion of the ion guide 1. In another mode of operation at least a portion of the ion guide 1 may be operated as an ion mobility spectrometer or separator section. Ions are preferably separated temporally according to their ion mobility as they pass through or around the ion mobility spectrometer or separator section of the ion guide 1.

According to the preferred embodiment one or more transient DC potentials or voltages or one or more transient DC potential or voltage waveforms are preferably superimposed on or applied to at least one section of the ion guide 1. The superimposed transient DC potentials or voltages preferably propel or drive ions around at least a portion of the closed-loop ion guide 1. Ions are preferably caused to move in the same direction that the one or more transient DC potentials or voltages are progressively applied to the electrodes comprising the ion guide 1.

The ion guide 1 preferably comprises an ion injection means 2 which is preferably arranged to introduce a pulse or stream of ions into the closed-loop ion guide 1. The ion guide 1 preferably also further comprises an ion ejection means 3 which is preferably arranged to divert at least some of the ions out from the closed-loop ion guide 1. Ions which are ejected from the ion guide 1 may be subjected to further analysis and/or may be detected by an ion detector (not shown).

According to the preferred embodiment the closed-loop ion guide 1 comprises a stacked ring ion guide comprising a plurality of electrodes. Each electrode preferably comprises an aperture through which ions are transmitted in use. The apertures of the electrodes forming the closed-loop ion guide 1 are preferably all the same size. In other embodiments at least 60%, 65%, 70%, 75%, 80%, 85%, 90% or 95% of the electrodes have apertures that are substantially the same size.

Adjacent electrodes of the ion guide 1 are preferably connected to opposite phases of an AC or RF voltage supply. An AC or RF voltage is preferably applied to the electrodes of the ion guide 1 and preferably causes ions to be confined radially within the ion guide 1 within a radial pseudo-potential well.

The one or more transient DC potentials or voltages or one or more transient DC potential or voltage waveforms which are preferably applied to the electrodes of the ion guide 1 preferably cause one or more potential hills or barriers to be formed which effectively move or rotate along and/or around the length of the ion guide 1. The one or more transient DC potentials or voltages or one or more transient DC potential or voltage waveforms are preferably progressively applied to a succession of electrodes which form the ion guide 1 such that the one or more potential hills or barriers move along or around the length or circuit of the ion guide in a certain direction. Ions are preferably propelled or driven along or around the ion guide 1 in the same direction or sense that the potential hills or barriers are progressively applied to the electrodes.

The ion guide 1 is preferably provided in a vacuum chamber that is preferably maintained, in use, at a pressure within the range $10^{-3}$ to 10 mbar. According to less preferred embodiments, the vacuum chamber may be maintained at a pressure greater than 10 mbar up to a pressure at or near atmospheric pressure. According to less preferred embodiments, the vacuum chamber may be maintained at a pressure below $10^{-3}$ mbar.

The presence of gas within the ion guide 1 preferably results in ion-molecule collisions which preferably cool the ions so that their average kinetic energies are reduced. If the kinetic energies of the ions are reduced then the ions will collapse towards the central axis of the ion guide 1.

Alternatively, if collisions between ions and gas molecules are arranged to be relatively energetic then the ions will be heated so that their internal energy is increased. If the heating is sufficient then complex ions, such as biological molecules including proteins, may unfold or at least partially unfold, thereby increasing their cross-sectional area. If complex molecules unfold or partially unfold then this may then result in their ion mobility being reduced. If the ions are further heated then the ions may be caused to fragment into fragment or daughter ions.

If ion-molecule collisions are sufficiently frequent then the buffer gas will impose a viscous drag on the movement of ions. If the viscous drag of the gas and the amplitude and average velocity of the one or more potential hills or barriers of the one or more transient DC potentials or voltages or one or more transient DC potential or voltage waveforms applied to the electrodes is set appropriately, then ions will, from time to time, slip over a potential hill or barrier which is being translated around the ion guide 1. Under these conditions ions will start to separate according to their ion mobility. The lower the mobility of an ion the more likely the ion will be to slip over a potential hill or barrier which is being translated or rotated around a portion of the ion guide 1. As a result ions of different ion mobility will preferably be transported at different average velocities around the ion guide 1 and hence will become separated temporally.

One or more stages or sections of the closed-loop ion guide 1 may comprise an ion mobility spectrometer or separator section wherein ions are preferably temporally separated according to their ion mobility. According to another embodiment ions may be induced to unfold or partially unfold in one or more stages or sections of the closed-loop ion guide 1. According to another embodiment ions may be induced to fragment in one or more stages or sections of the closed-loop ion guide 1. Further embodiments are contemplated wherein various different permutations or combinations of stages or sections may be provided. So, for example, an ion mobility separation stage may be followed by a ion fragmentation stage.

If buffer gas is provided within one or more sections of the closed-loop ion guide 1, then ions will experience a degree of resistance to ion motion. Therefore, in order to assist ions in being circulated around the closed-loop ion guide 1 a number of times, means for propelling or driving ions around at least a portion or section of the ion guide 1 are preferably provided. According to the preferred embodiment one or more transient DC potentials or voltages or one or more transient DC potential or voltage waveforms may be applied to the electrodes forming the ion guide 1 in order to propel at least some ions substantially continuously around the closed-loop ion guide 1 until it is desired to eject the ions from the ion guide 1.

Ions may be urged along or around at least a portion of the closed-loop ion guide 1 by superimposing a constant axial DC voltage gradient along at least a portion of the ion guide 1. However, in a closed-loop, the integral of the axial DC voltage gradient around the loop should equal zero. Therefore, if a DC voltage gradient is applied across or along a section of the ion guide 1 in order to urge ions in one direction then at some other point around the closed-loop ion guide 1 where the circuit connects to itself ions will experience a DC voltage gradient which acts to oppose the onward transmission of ions.

According to the preferred embodiment one or more transient DC potentials or voltages or one or more transient DC potential or voltage waveforms may be applied to the electrodes forming the ion guide 1 at the point where ions experience a DC voltage gradient which otherwise acts to oppose the onward transmission of ions. The application of the transient DC voltages or potentials to the ion guide 1 at this point preferably helps to propel ions over, across or against the DC voltage gradient which would otherwise oppose the onward transmission of ions.

According to another embodiment the ion guide 1 may comprise a plurality of plate electrodes arranged generally or substantially in the plane in which the ions travel in use through or along the length of the ion guide 1. The ion guide 1 may comprise upper and/or lower plate electrodes. The upper and/or lower plate electrodes may be axially segmented. One or more transient DC potentials or voltages or one or more transient DC potential or voltage waveforms may be applied to the segmented upper and/or lower plate electrodes in order to urge at least some ions along or around at least a portion of the length or circuit of the ion guide 1. Opposite phases of an AC or RF voltage are preferably applied to adjacent plate electrodes disposed between the upper and lower plate electrodes so that ions are preferably confined in a radial direction within the ion guide. One or more transient DC potentials or voltages or one or more transient DC potential or voltage waveforms may also be applied to the plate electrodes arranged between the upper and lower plate electrodes.

According to a less preferred embodiment the closed-loop ion guide 1 may comprise a segmented rod set ion guide. Adjacent rods are preferably connected to opposite phases of an AC or RF supply. One or more transient DC potentials or voltages or one or more transient DC potential or voltage waveforms are preferably applied to one or more of the rod segments so that one or more potential hills or barriers are formed which preferably move around and along the length of the ion guide. The one or more transient DC potentials or voltages or one or more transient DC potential or voltage waveforms are preferably progressively applied to a succession of the rod segments such that the one or more potential hills or barriers preferably move along the axis of the ion guide in the direction in which the ions are to be propelled or driven.

According to a less preferred embodiment the ion guide 1 may comprise a combination of a rod set and a plurality of ring electrodes which surround the rod set so that the rod electrodes are provided within the apertures of the ring electrodes so as to form a ring pole arrangement. Adjacent rod electrodes are preferably connected to the opposite phases of an AC or RF supply. One or more transient DC potentials or voltages or one or more transient DC potential or voltage waveforms are preferably applied to the ring electrodes so that one or more transient DC potential hills or barriers are created within the ion guiding region formed within the rod set. The one or more transient DC potentials or voltages or one or more transient DC potential or voltage waveforms are preferably progressively applied to a succession of the ring electrodes such that the one or more potential hills or barriers move along the axis of the ion guide or around the ion guide in the direction in which it is desired to propel or drive ions.

Figure 2:
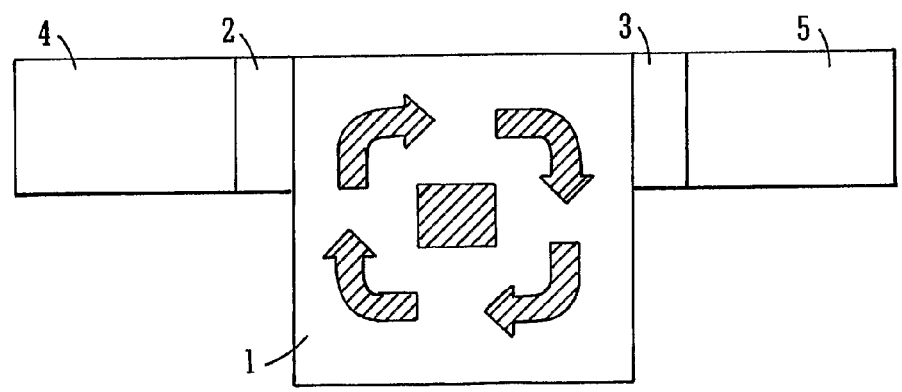
FIG. 2 shows a mass spectrometer comprising a closed-loop ion guide according to the preferred embodiment.

A mass spectrometer according to a preferred embodiment of the present invention is shown in FIG. 2. The mass spectrometer preferably comprises an ion source 4, an ion gate or device 2 for injecting ions into a closed-loop ion guide 1, an ion gate or device 3 for ejecting ions from the closed-loop ion guide 1 and a mass analyser 5 which is preferably arranged downstream of the ion guide 1. Ions which are injected into the closed-loop ion guide 1 preferably make one or more passes or circuits around the closed-loop ion guide 1. At least some ions are preferably ejected from the ion guide 1 by the ion gate or device 3 and the ions are preferably onwardly transmitted to the mass analyser 5 where the ions are then mass analysed.

The ion source 4 may comprise a pulsed ion source such as a Laser Desorption Ionisation ("LDI") ion source, a matrix Assisted Laser Desorption Ionisation ("MALDI") ion source or a Desorption Ionisation on Silicon ("DIOS") ion source. Alternatively, the ion source 4 may comprise a continuous ion source. If the ion source 4 comprises a continuous ion source then an ion trap for storing ions and periodically releasing ions may be provided upstream of the closed-loop ion guide 1. The continuous ion source may comprise an Electrospray Ionisation ("ESI") ion source, an Atmospheric Pressure Chemical Ionisation ("APCI") ion source, an Electron Impact ("EI") ion source, an Atmospheric Pressure Photon Ionisation ("APPI") ion source, a Desorption Electrospray Ionisation ("DESI") ion source, a Chemical Ionisation ("CI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source. The ion source 4 may comprise another form of continuous or pseudo-continuous ion source.

One or more mass selective stages such as a multipole rod set mass filter, an ion funnel, a quadrupole mass filter, a Wein filter, a Time of Flight mass filter or mass analyser, or a magnetic sector mass filter or mass analyser may be provided upstream and/or downstream of the closed-loop ion guide 1.

One or more AC or RF ion guides such as a multipole rod set ion guide, a stacked ring ion guide, an ion tunnel ion guide, an ion funnel ion guide or a stacked plate ion guide may be provided downstream of the ion source 4 and preferably upstream of the ion gate or device 2 which is preferably arranged to inject ions into the preferred closed-loop ion guide 1.

The mass analyser 5 preferably comprises an orthogonal acceleration Time of Flight mass analyser. However, according to other embodiments the mass analyser 5 may comprise an axial acceleration Time of Flight mass analyser, a quadrupole mass analyser, a 3D quadrupole ion trap, a linear quadrupole ion trap, a quadrupole mass filter, a magnetic sector mass analyser, an ion cyclotron resonance mass analyser or an orbitrap mass analyser. The mass analyser 5 may comprise variations of the aforementioned types of mass analyser employing Fourier transforms of mass dependant resonance frequencies.

According to one embodiment the means 2 for introducing or injecting ions into the closed-loop guide 1 and/or the means 3 for removing or ejecting ions from the closed-loop ion guide 1 may comprise a stacked plate ion guiding section comprising multiple ion entry and/or ion exit ports. The ion guiding section may be arranged so as to allow a continuous streams of ions to be merged, divided or switched from one ion guiding path or channel to another.

According to an embodiment of the present invention the means for introducing ions 2 into the closed-loop ion guide and/or the means for removing or selecting ions 3 from the closed-loop ion guide 1 may form an integral part of the closed-loop ion guide 1. The ion selection device 2,3 for introducing ions into the closed-loop ion guide 1 and/or ejecting ions from the closed-loop ion guide 1 may be maintained at substantially the same pressure as the closed-loop ion guide 1.

Figure 3B:
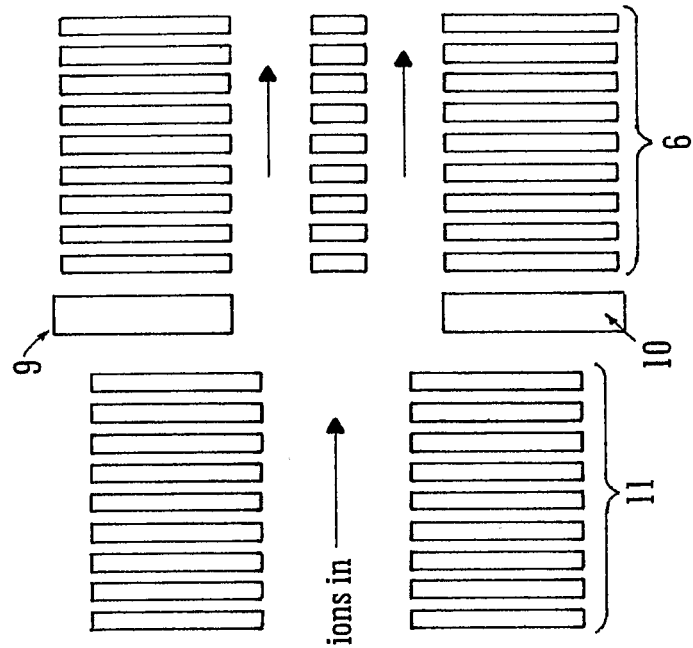
FIG. 3A shows a section through a device for introducing ions into a preferred closed-loop ion guide and FIG. 3B shows a section through a device for removing ions from a preferred closed-loop ion guide.
Figure 3A:
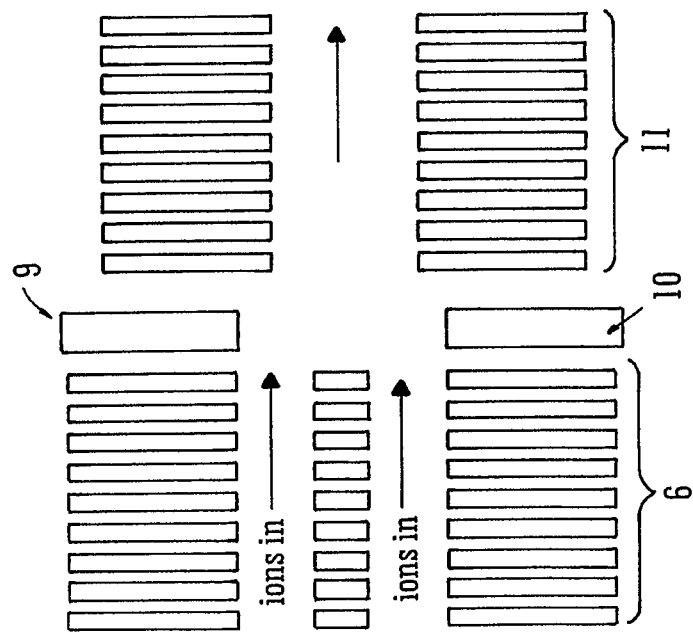

FIG. 3A shows a section through a device which may be used to introduce or inject ions into a closed-loop ion guide 1. FIG. 3B shows a section through a device which may be used to remove or eject ions from a closed-loop ion guide 1.

FIG. 4A shows a perspective view of a device similar to that shown in FIGS. 3A and 3B which may be used either to introduce ions into a closed-loop ion guide 1 or to remove ions from a closed-loop ion guide 1. The device as shown in FIG. 4A preferably a first section comprising a plurality of ring electrodes 6 each having a two circular apertures as shown in FIGS. 4A, 4D and 4E. The separation or spacing between the two apertures 7,8 may remain substantially constant along the length of the first section (as shown, for example, in FIG. 3A). Alternatively, according to an embodiment as shown in FIG. 4D one of the electrodes 6 may comprise two apertures 7,8 which are spaced closer than the apertures in the other electrodes. The electrode 6 having two apertures which are spaced closer together than the apertures in the other electrodes is preferably arranged adjacent to a pair or deflection electrodes 9,10.

FIGS. 3A and 4A show a pair of deflection electrodes 9,10 arranged downstream of the first section. Downstream of the deflection electrodes 9,10 a second section of the ion guide is preferably provided. The second section of the ion guide preferably comprises a plurality of ring electrodes 11. Each ring electrode 11 preferably comprises a single aperture as shown in 4B. The apertures of the ring electrodes 11 in the second section are preferably substantially the same size.

According to a less preferred embodiment the electrodes 6 in the first section and the electrodes 11 in the second section may comprise non-circular apertures. For example, the electrodes 6,11 may comprise square or triangular apertures.

According to the preferred embodiment adjacent electrodes in the first and/or second sections are preferably connected to opposite phases of an AC or RF supply. The AC or RF voltage applied to the electrodes 6,11 preferably causes ions to be confined radially within a pseudo-potential well formed within the ion guide. The AC or RF voltage may also be applied to the deflection electrodes 9,10 in order to confine ions within the central section of the device.

One or more transient DC potentials or voltages or one or more transient DC potential or voltage waveforms are preferably applied to one or more of the electrodes in the first and/or second sections so that one or more potential hills or barriers are preferably created which are preferably translated in use along the length of the first and/or second sections of the ion guide 1. The one or more transient DC potentials or voltages or one or more transient DC potential or voltage waveforms are preferably progressively applied to a succession of electrodes such that the one or more potential hills or barriers preferably move along the axis of the ion guide 1 in the direction in which ions are desired to be propelled or driven.

Other embodiments are contemplated wherein the electrodes 6 in the first section may comprise more than two apertures so that, for example, three or more input ion guiding channels may be provided thereby enabling ions from various different channels to be injected into the closed-loop ion guide 1 as desired.

According to the preferred embodiment the two deflection electrodes 9,10 preferably have DC voltages applied to them in use which preferably cause an ion beam passing past the deflection electrodes 9,10 to be diverted or deflected in a particular direction. For example, the device shown in FIGS. 3B and 4A may be arranged so that ions pass from one section of the ion guide comprising electrodes having a single aperture pass the deflection electrodes 9,10 and into one of two ion guiding channels provided in another section of the ion guide. Ions are therefore deflected or diverted by the deflection electrodes 9,10 into an ion guiding path arranged within one of two apertures 7,8 of a section of the ion guide 1.

FIG. 3B shows an embodiment wherein ions within the closed-loop ion guide 1 may be ejected from the ion guide into one of two channels. The two deflection electrodes 9,10 are preferably arranged to have DC voltages applied to them in order to deflect an ion beam into one of the two channels provided in the electrode section arranged downstream of the deflection electrodes 9,10. Similarly, with reference to FIG. 3A appropriate DC voltages may be applied to the deflection electrodes 9,10 in order to guide ions from an input ion channel into the closed-loop ion guide.

A deflection lens is preferably used to inject ions into and/or to eject ions out from the closed-loop ion guide and preferably comprises a pair of electrodes 9,10. However, other embodiments are contemplated wherein a deflection lens may be provided which comprises three or more electrodes which are arranged to divert or deflect an ion beam. The aperture formed by the deflection lens or the deflection electrodes 9,10 is preferably circular and each deflection electrode 9,10 preferably comprises a semi-circular aperture. However, other embodiments are contemplated wherein the deflection lens may comprise one or more deflection electrodes which together form a non-circular aperture.

Various simulations were performed using a computer model of an ion guide comprising two sections separated by a pair of deflection electrodes. The simulation was performed using a model of an ion guide wherein ions were confined within a single ion guiding region. The ions were then diverted or deflected by two deflection electrodes into one of two ion guiding channels provided within another section of the ion guide arranged downstream of the deflection electrodes. The diameter of the apertures of the electrodes in the upstream section of the ion guide comprising a single ion guiding channel were modelled as being 5 mm. All the electrodes of the ion guide were modelled as being 0.5 mm thick and arranged with an inter-electrode spacing of 1 mm.

The electrodes in the downstream section of the ion guide comprising two ion guiding channels were modelled as comprising electrodes having two apertures which were each 4 mm in diameter. The two apertures were modelled as being spaced 5 mm apart (centre-to-centre) except for the electrode arranged closest to the two deflection electrodes. The electrode arranged closest to the two deflection electrodes was modelled as having two apertures each 4 mm in diameter which were spaced 4.4 mm apart (centre-to-centre).

The two deflection electrodes were modelled as being 1 mm thick and the central aperture formed by the two deflection electrodes was modelled as being 5 mm in diameter. The two deflection electrodes were modelled as being spaced 1 mm away from the other electrodes.

FIGS. 5A-5D shows SIMION computer simulations of ion trajectories through an ion guide as described above. In the SIMION computer simulations the ions moved from right to left in the figures. The SIMION model used took account of collisions between ions with buffer gas. For all of the simulated trajectories shown in FIGS. 5A-5D the buffer gas was modelled as being Argon at a pressure of 0.5 mbar.

An RF voltage was modelled as being applied to the electrodes in the upstream and downstream sections of the ion guide. The RF voltage applied to the electrodes was modelled as having an amplitude of 200 V peak to peak and a frequency of 2.7 MHz.

A transient DC voltage having an amplitude of 10 V was modelled as being applied to consecutive pairs of electrodes for a duration of 10 μs before being applied to the next neighbouring pair of electrodes. The electrodes upstream of the deflection electrodes were also modelled as being maintained at a constant DC bias of +15 V whilst the electrodes arranged downstream of the two deflection electrodes were modelled as being held at a DC bias of 0V. The electrode closest to the two deflection electrodes and arranged downstream of the deflection electrodes was modelled as being held at a potential of 2 V. The two deflection electrodes were modelled as being held at potentials of 18 V and 7 V.

Figure 5A:
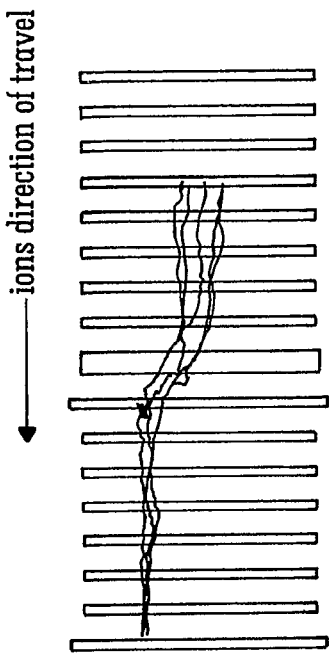
FIG. 5A shows a simulation of the trajectories of ions having a mass to charge ratio of 100 as they pass through a device for introducing or removing ions maintained at a pressure of 0.5 mbar.

FIG. 5A shows the trajectories of five ions having mass to charge ratios of 100 through the section of the ion guide. The ions had starting positions in the range ±1 mm from the central axis of the ion guide. The ions were successfully directed into an ion guiding region or channel defined within one of the apertures in the section of the ion guide arranged downstream of the two deflection electrodes.

Figure 5B:
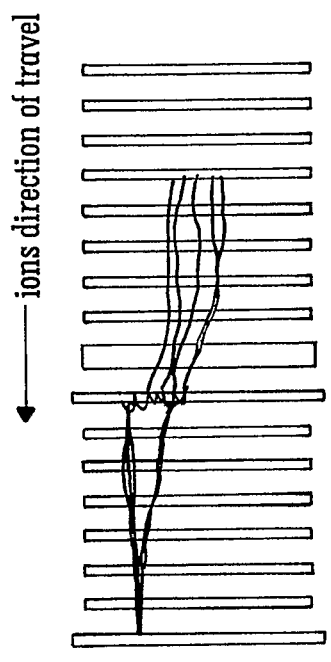
FIG. 5B shows a simulation of the trajectories of ions having a mass to charge ratio of 100 as they pass through a device for introducing or removing ions maintained at a pressure of 0.5 mbar wherein the voltages applied to two deflection electrodes were swapped over so that ions were transmitted into a different channel.

It will be apparent that the ion beam may be guided into the other of the two channels in the ion guide by altering or reversing the DC potentials applied to the two deflection electrodes. FIG. 5B shows the result of a simulation when the potentials applied to the two deflection electrodes were swapped or reversed. Ions were then diverted into the other of the two channels within the ion guide section arranged downstream of the two deflection electrodes.

Figure 5C:
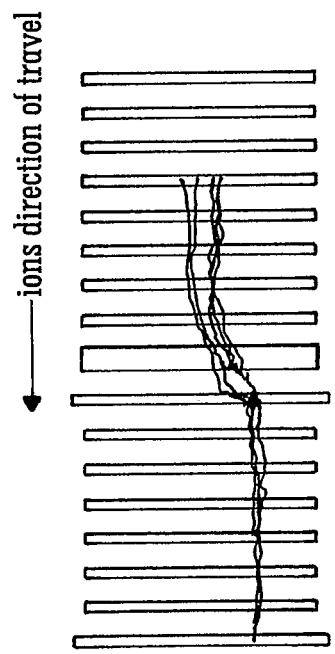
FIG. 5C shows a simulation of the trajectories of ions having a mass to charge ratio of 1000 as they pass through a device for introducing or removing ions maintained at a pressure of 0.5 mbar
Figure 5D:
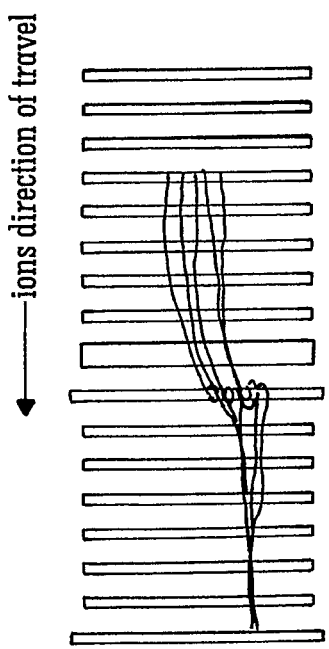
FIG. 5D shows a simulation of the trajectories of ions having a mass to charge ratio of 1000 as they pass through a device for introducing or removing ions maintained at a pressure of 0.5 mbar wherein the voltages applied to two deflection electrodes were swapped over so that ions were transmitted into a different channel.
Figure 6A:
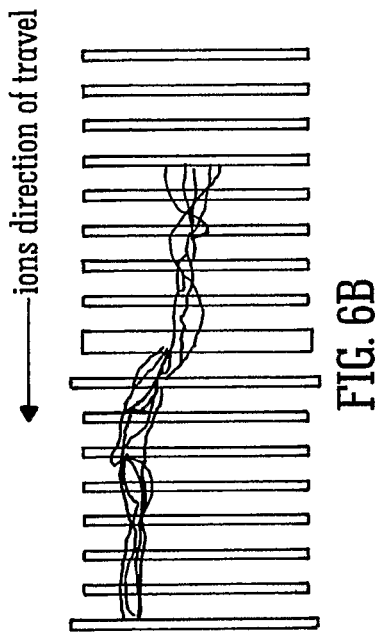
FIG. 6A shows a simulation of the trajectories of ions having a mass to charge ratio of 100 as they pass through a device for introducing or removing ions maintained at a pressure of $1 \times 10^{-2}$ mbar.
Figure 6B:
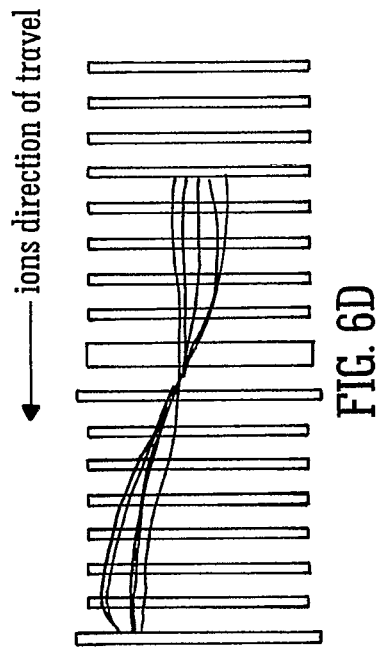
FIG. 6B shows a simulation of the trajectories of ions having a mass to charge ratio of 100 as they pass through a device for introducing or removing ions maintained at a pressure of $1 \times 10^{-2}$ mbar wherein the voltages applied to two deflection electrodes were swapped over so that ions were transmitted into a different channel.
Figure 6C:
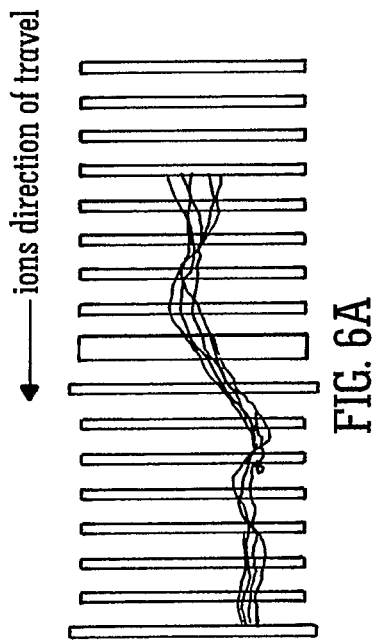
FIG. 6C shows a simulation of the trajectories of ions having a mass to charge ratio of 1000 as they pass through a device for introducing or removing ions maintained at a pressure of $1 \times 10^{-2}$ mbar and FIG. 6D shows a simulation of the trajectories of ions having a mass to charge ratio of 1000 as they pass through a device for introducing or removing ions maintained at a pressure of $1 \times 10^{-2}$ mbar wherein the voltages applied to two deflection electrodes were swapped over so that ions were transmitted into a different channel.
Figure 6D:
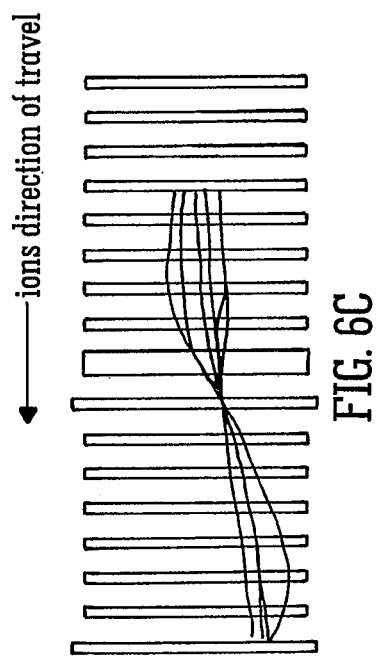

FIG. 5C shows the result of a simulation under conditions similar to those used for the simulation as described above in relation to FIG. 5A but wherein the mass to charge ratio of the ions was increased to 1000. FIG. 5D likewise shows the result of a simulation under conditions which were similar to those used for the simulation as described above in relation to FIG. 5B except that the mass to charge ratio of the ions was increased to 1000. It is apparent from FIGS. 5A-5D that the device is able to divert or deflect ions into a desired channel irrespective of the mass to charge ratio of the ions.

FIGS. 6A-6D show the results of simulations under simulated conditions which were similar to those which were modelled and described above in relation to FIGS. 5A-5D except that the pressure of the Argon gas was modelled as being reduced to $1 \times 10^{-2}$ mbar and the amplitude of the transient DC voltages applied to the electrodes was modelled as being reduced to 1 V. All other parameters were the same as for the simulations described above in relation to FIGS. 5A-5D. It is apparent from FIGS. 6A-6D that the ions were directed into a desired channel under simulated conditions wherein the gas pressure was relatively low and the amplitude of the transient DC voltage or potential applied to the electrodes was also relatively low.

A closed-loop ion guide according to the preferred embodiment may have an axial DC potential gradient at some point along the length of the ion guide which acts to oppose the onward transmission of ions. In order to make ions complete multiple circuits around the closed-loop ion guide means are preferably provided to force, propel or urge ions across the potential gradient which would otherwise potentially oppose the onward transmission of ions.

Figure 7:
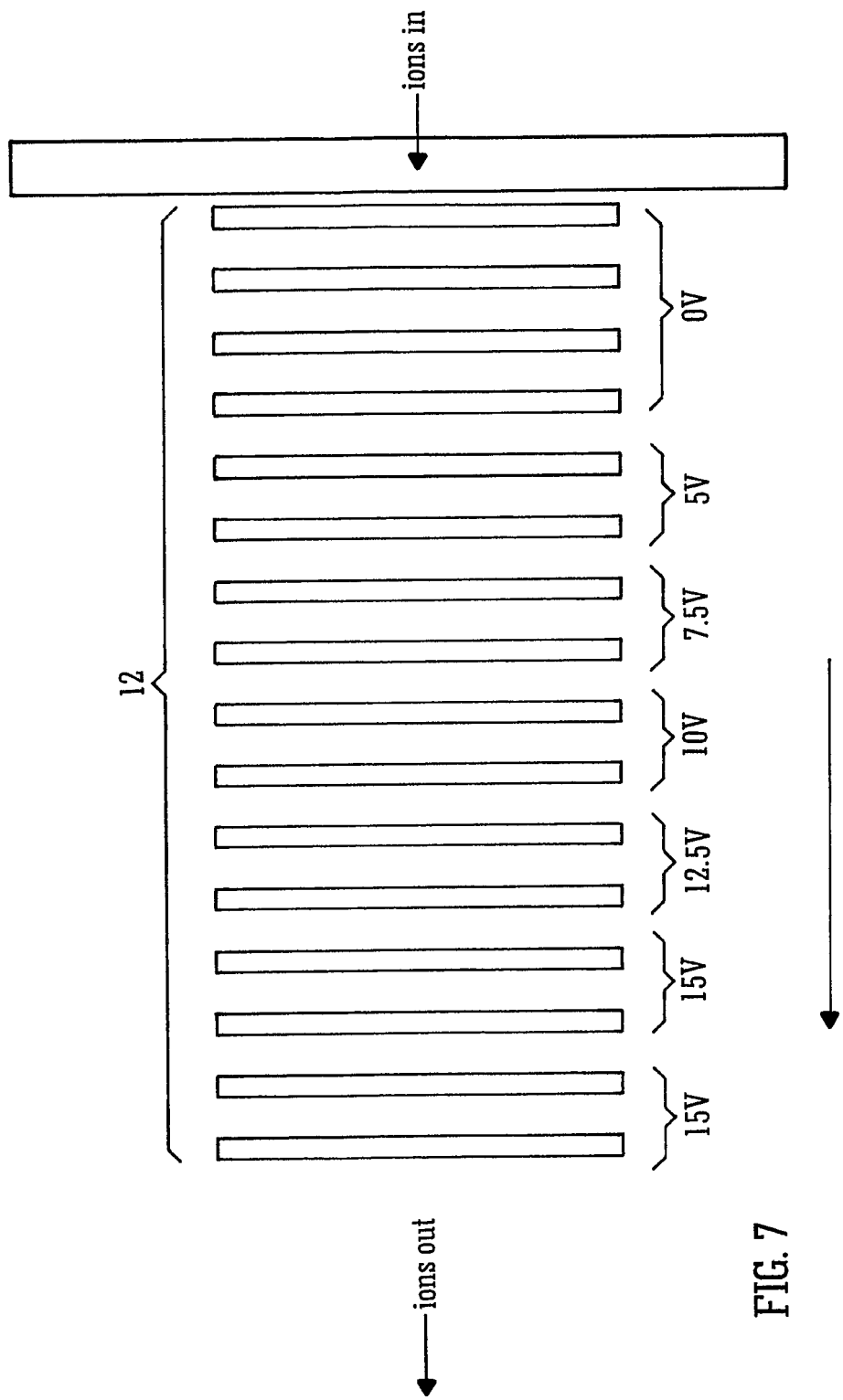
FIG. 7 shows a schematic of a section of a preferred ion guide wherein ions are driven forwards so as to overcome a potential difference which otherwise acts to oppose the onward transmission of ions.

FIG. 7 shows a section of an ion guide 12 which was modelled to show how ions may be forced, propelled or urged against a DC potential gradient which would otherwise act to oppose the onward transmission of ions. In the ion guide section 12 as shown in FIG. 7 ions were modelled as being transmitted from the right hand side of the ion guide to the left hand side. The transmission of ions is opposed by a DC potential gradient which increases from right to left. The height of the potential gradient was modelled as being 15 V. The electrodes of the ion guide section 12 were modelled as having apertures which were 5 mm in diameter. A buffer gas was modelled as being present and which comprised Argon maintained at a pressure of 0.5 mbar.

An RF voltage was modelled as being applied to the electrodes of the ion guide section 12 in order to confine ions radially within the ion guide section 12. The RF voltage was modelled as having an amplitude of 200 V peak to peak and having a frequency of 2.7 MHz.

A transient DC voltage having an amplitude of 25 V was modelled as being applied to consecutive pairs of electrodes for a duration of 10 μs before being applied to the neighbouring pair of electrodes.

Figure 8A:
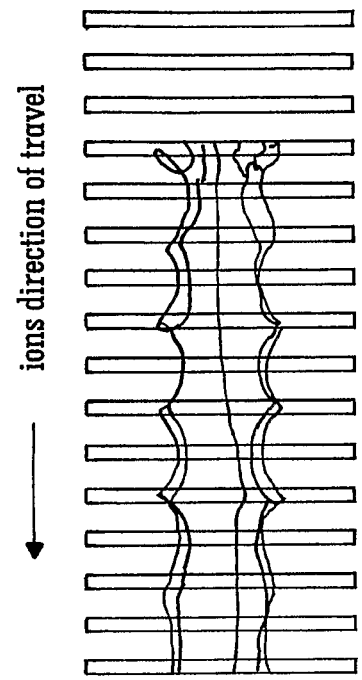
FIG. 8A shows a simulation of the trajectories of ions having a mass to charge ratio of 100 passing through a potential recovery section of a preferred ion guide maintained at a pressure of 0.5 mbar
Figure 8B:
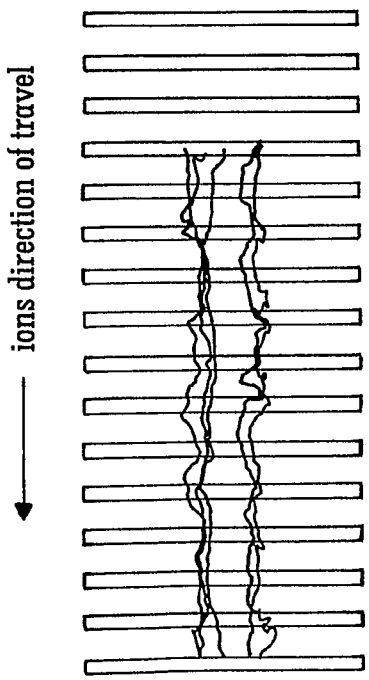
FIG. 8B shows a simulation of the trajectories of ions having a mass to charge ratio of 1000 passing through a potential recovery section of a preferred ion guide maintained at a pressure of 0.5 mbar.

FIG. 8A shows the result of a SIMION simulation of ions having mass to charge ratios of 100 and passing through the ion guide section 12 as shown in FIG. 7. FIG. 8B shows the result of a SIMION simulation of ions having a mass to charge ratio of 1000 and passing through the ion guide section 12. In both cases the ions were modelled as having starting positions of ±1 mm from the central axis of the ion guide section 12. It is apparent from FIGS. 8A and 8B that the transient DC voltage applied to the electrodes of the ion guide section 12 is effective at transporting or forcing ions along the ion guide section 12 against the opposed DC potential gradient.

Figure 9B:
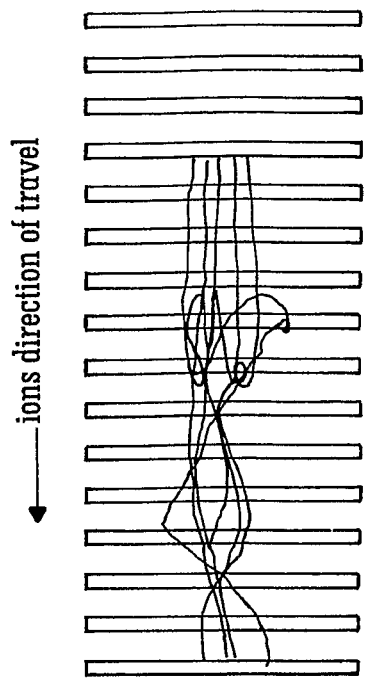
FIG. 9A shows a simulation of the trajectories of ions having a mass to charge ratio of 100 passing through a potential recovery section of a preferred ion guide maintained at a pressure of $1 \times 10^{-2}$ mbar and FIG. 9B shows a simulation of the trajectories of ions having a mass to charge ratio of 1000 passing through a potential recovery section of a preferred ion guide maintained at a pressure of $1 \times 10^{-2}$ mbar.
Figure 9A:
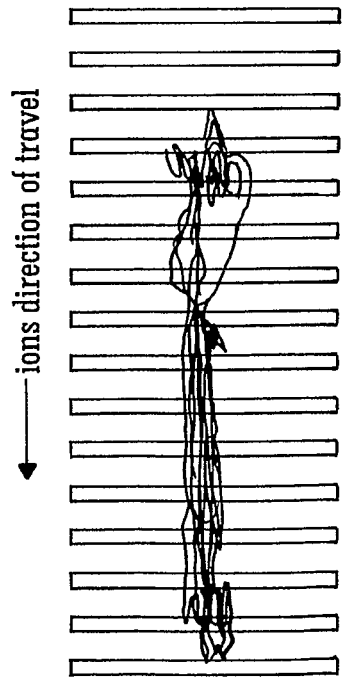

FIG. 9A shows the result of a similar simulation to that shown with respect to FIG. 8A but wherein the gas pressure of the Argon gas was modelled as being reduced to $1 \times 10^{-2}$ mbar. FIG. 9B shows the result of a similar simulation to that shown with respect to FIG. 8B but also at a reduced gas pressure of Argon of $1 \times 10^{-2}$ mbar. In the simulations shown in FIGS. 9A and 9B the amplitude of the transient DC voltage applied to the electrodes of the ion guide section 12 was reduced from 25 V to 15V and the RF voltage applied to the electrodes was increased from 200V peak to peak to 260V peak to peak. It is apparent from FIGS. 9A and 9B that ions can be urged across the opposed DC potential gradient at lower pressures by applying transient DC voltages or potentials to the electrodes which have a lower amplitude.

Various further embodiments of the present invention are contemplated and will now be described with reference to FIGS. 10A-10C. According to these further embodiments an ion guide is provided comprising means for introducing ions into the closed-loop ion guide and means for removing ions from the closed-loop ion guide. The means for introducing ions into the closed-loop ion guide and the means for removing ions from the closed-loop ion guide are both represented schematically in FIGS. 10A-10C by a means 13 for switching ion trajectories.

Figure 10A:
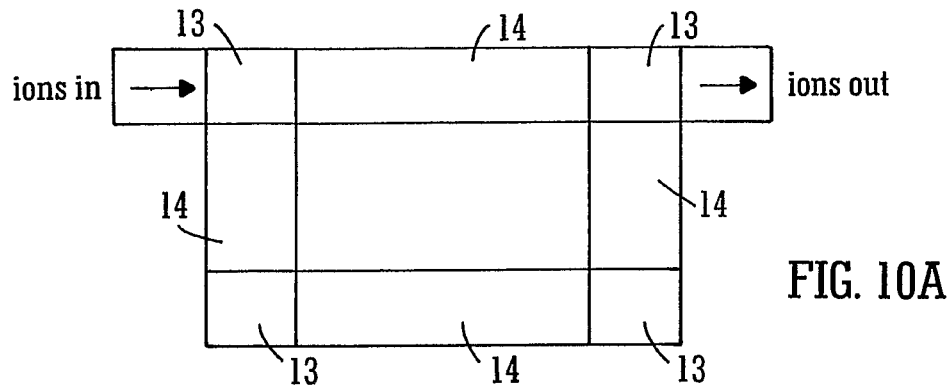
FIG. 10A shows an embodiment of a closed-loop ion guide incorporating means for introducing and removing ions from the closed-loop ion guide.
Figure 10B:
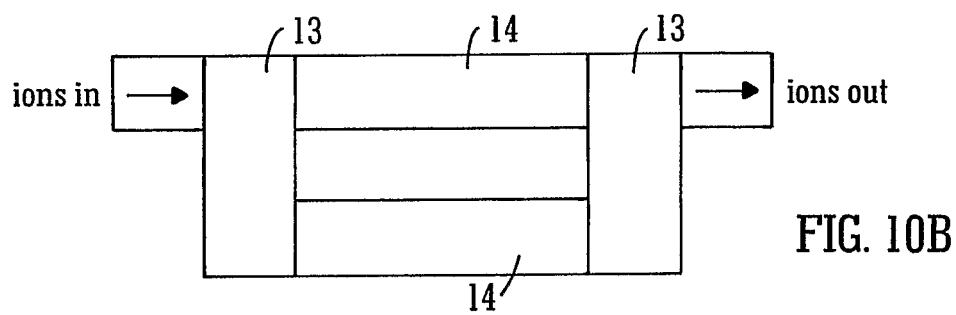
FIG. 10B shows another embodiment of a closed-loop ion guide incorporating means for introducing and removing ions from the closed-loop ion guide and FIG. 10C shows a further embodiment of a closed-loop ion guide incorporating means for introducing and removing ions from the closed-loop ion guide.
Figure 10C:
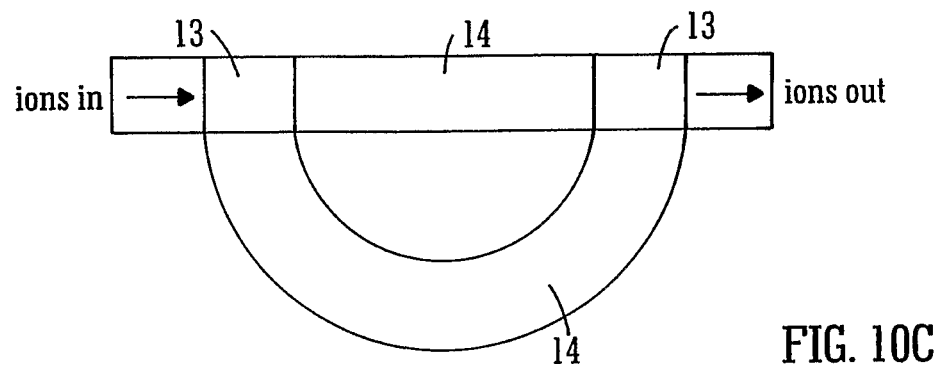

In the embodiments shown in FIGS. 10A-10C the ions are transported in a clockwise direction around the closed-loop ion guide by applying a transient DC potential to successive electrodes in each ion guide section 14 which comprises the closed-loop ion guide. Other embodiments are contemplated wherein ions may be transported in an anti-clockwise direction around the closed-loop ion guide. In the embodiment shown in FIG. 10A ions are redirected from one ion guiding channel to another in some of the ion switching sections 13. In other sections ions are transmitted from one ion guide section 14 to another.

The ion guide sections 14 may comprise either a straight or a curved ion guiding section. For example, in the embodiment shown in FIG. 10C one of the ion guide sections 14 comprises a curved ion guiding path.

In the embodiments shown in FIGS. 10A-10C the ion switching sections 13 preferably all comprise means for introducing ions into and/or withdrawing ions from the closed-loop ion guide. The ion switching sections 13 preferably also direct ions from one section of closed-loop ion guide to the next section. Embodiments are also contemplated, however, wherein ions may be introduced and/or withdrawn from the ion guide sections 14.

According to the embodiments shown and described with reference to FIGS. 10A-10C, the ion selection and/or redirection devices or sections 13 are preferably maintained at substantially the same pressure as the ion guide sections 14.

Embodiments are contemplated wherein one or more of the ion guide sections 14 may be maintained at a pressure such that when ions are accelerated into the ion guide section 14 then the ions are preferably caused to fragment by Collision Induced Decomposition ("CID") into fragment or daughter ions.

According to an embodiment one or more of the ion guide sections 14 may be maintained at a pressure which is optimum for ions to be separated according to their ion mobility. Accordingly, one or more sections 14 of the ion guide may comprise an ion mobility separation section.

If a portion of the ion guide is operated as a collision, fragmentation or reaction cell then the ion guide section may preferably be maintained, in use, at a pressure within the range $10^{-3}$ to $10^{-1}$ mbar. If a portion of the ion guide is operated as an ion mobility separator then the ion guide section may preferably be maintained, in use, at a pressure within the range $10^{-1}$ to 10 mbar.

Figure 11A:
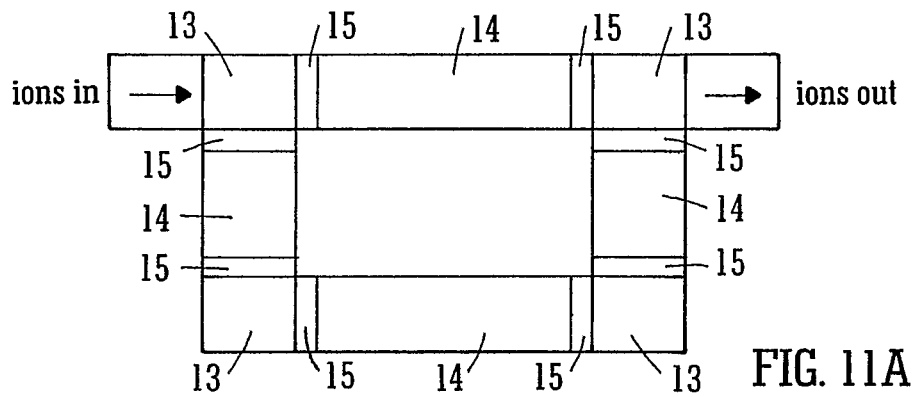
FIG. 11A shows an embodiment of a closed-loop ion guide incorporating means for introducing and removing ions from the closed-loop ion guide and differential pumping apertures allowing separation of the ion introduction and removal devices from an ion mobility separator stage.
Figure 11B:
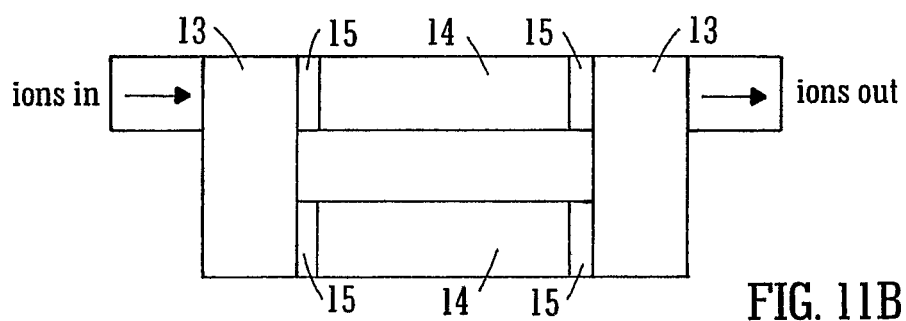
FIG. 11B shows another embodiment of a closed-loop ion guide incorporating means for introducing and removing ions from the closed-loop ion guide and differential pumping apertures allowing separation of the ion introduction and removal devices from an ion mobility separator stage.
Figure 11C:
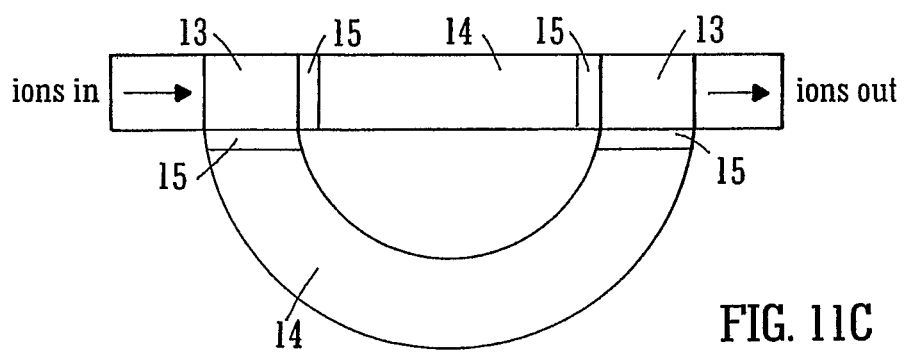
FIG. 11C shows a further embodiment of a closed-loop ion guide incorporating means for introducing and removing ions from the closed-loop ion guide and differential pumping apertures allowing separation of the ion introduction and removal devices from an ion mobility separator stage.

FIGS. 11A-11C illustrate yet further embodiments of the present invention wherein differential pumping apertures 15 are provided between ion guide sections 14 and the means 13 for introducing, withdrawing or redirecting ions. According to this embodiment the provision of differential pumping apertures 15 preferably enables different sections of the closed-loop ion guide to be maintained at different pressures. For example, one or more of the ion guide sections 14 may be maintained at a relatively high pressure whilst other ion guide sections 14 may be maintained at a relatively low pressure. The means for introducing, withdrawing or redirecting ions 13 may be maintained at a relatively higher or relatively lower pressure than that of the ion guide sections 14.

If pumping is applied to a section of the ion guide where a relatively low pressure is required, and gas is introduced into a section where a relatively high pressure is required, then a pressure differential will be established across the differential pumping aperture 15 which separates the two sections.

According to an embodiment one or more sections 14 of the closed-loop ion guide may be maintained, in use, at a pressure which is suitable for ion mobility separation whilst one or more other sections of the closed-loop ion guide may be maintained, in use, at a pressure which is suitable for collision induced unfolding of ions and/or collision induced fragmentation of ions.

Figure 12:
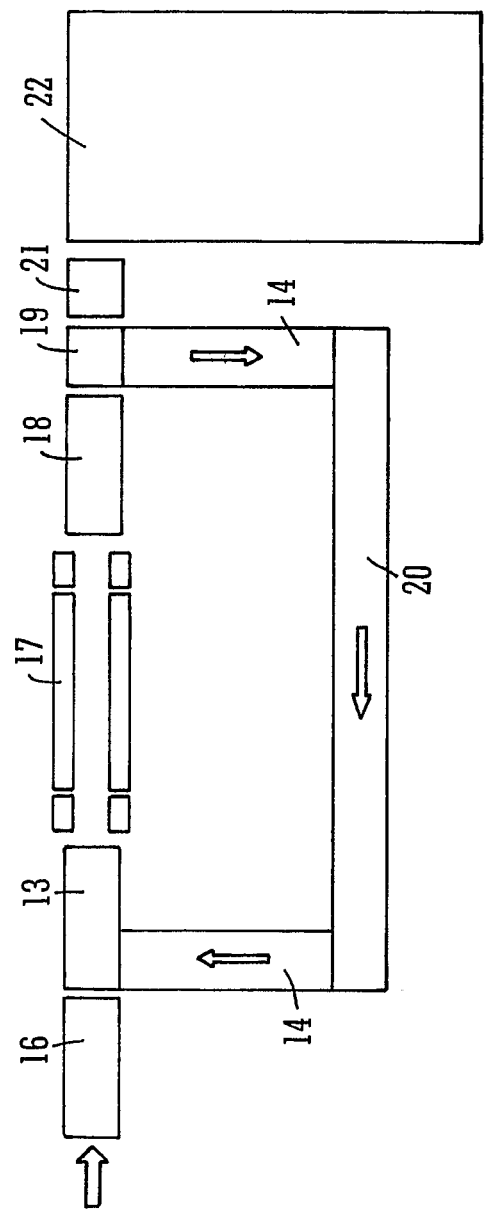
FIG. 12 shows an embodiment wherein a mass filter is included in the closed-loop ion guide.

FIG. 12 shows a further embodiment wherein a mass filter 17 is included in the closed-loop ion guide. Ions from an ion source (not shown) are preferably trapped in an ion trap 16. The ions preferably remain in the ion trap 16 whilst a previously released bunch of ions are analysed. A bunch or pulse of ions is then preferably released from the ion trap 16 and subsequently enter a merger cell 13. The ions then preferably pass from the merger cell 13 to a mass filter 17 which preferably comprises a quadrupole rod set mass filter. However, according to other embodiments the mass filter 17 may comprise another form of mass filter. The mass filter 17 may be operated in a number of different modes. The mass filter 17 may, for example, for operated in a lowpass, bandpass or highpass mass filtering mode of operation.

According to a preferred embodiment the mass filter 17 is preferably arranged to onwardly transmit parent or precursor ions having a particular mass to charge ratio and to substantially attenuate ions having other mass to charge ratios. The selected parent or precursor ions are then preferably onwardly transmitted to a collision, fragmentation or reaction cell 18. In a mode of operation the collision, fragmentation or reaction cell 18 is arranged to fragment the parent or precursor ions into a plurality of fragment or daughter ions. The resulting fragment or daughter ions then preferably pass from the collision, fragmentation or reaction device 18 to a diverter 19. The diverter 19 may be arranged either to transmit the fragment or daughter ions onwardly to an optional cooler cell 21 or alternatively to an ion guide 14 which preferably forms part of the closed-loop ion guide. The cooler cell 21 may be arranged to re-merge a pulsed ion beam into a substantially continuous ion beam. Ions are preferably onwardly transmitted from the cooler cell 21 to a mass analyser 22 which preferably comprises an orthogonal acceleration Time of Flight mass analyser.

If the fragment or daughter ions are passed by the diverter 19 to the ion guide 14, which forms part of the closed-loop ion guide, then the ions are then preferably onwardly transmitted to a return cell 20. Ions may preferably be stored in the return cell 20 until the merger cell 13 and the collision, fragmentation or reaction cell 18 are free of ions from the last pulse. The ions are then preferably transmitted from the return cell 20, via another ion guide section 14 to the merger cell 13. The fragment or daughter ions may then preferably be passed to the mass filter 17. The mass filter 17 may be arranged to select certain fragment or daughter ions for onward transmission and to substantially attenuate other ions having undesired mass to charge ratios. The selected fragment or daughter ions are then preferably passed to the collision, fragmentation or reaction cell 18 where the ions may be fragmented to form second generation fragment ions.

The second generation fragment ions then preferably pass from the collision, fragmentation or reaction cell 18 to the diverter 19. The diverter 19 may be arranged to either onwardly transmit the second generation fragment ions to the optional cooler cell 21 or to transmit the ions to the ion guide 14 which forms part of the closed-loop ion guide. It is apparent that if the second generation fragment ions are transmitted to the ion guide section 14 of the closed-loop ion guide then MS" experiments may be performed.

The merger cell 13 may or may not contain gas. The diverter cell 19 preferably controls whether an ion beam exits through one ion guiding channel or another ion guiding channel.

The return cell 20 may or may not contain a gas. One or more transient DC voltages or potentials or one or more transient DC voltage or potential waveforms may preferably be applied to the electrodes comprising the return cell 20 in order to help transport ions from the diverter cell 19 to the merger cell 13.

It is contemplated that the merger cell 13 and/or the collision cell 18 and/or the diverter cell 19 and/or the cooler cell 21 and/or the return cell 20 may be mounted on the same printed circuit board assembly either as stacked ring devices, stacked plate devices or a combination of both.

Various further embodiments of the present invention are contemplated. For example, embodiments are contemplated wherein different sections of the closed-loop ion guide may be maintained, in use, at pressures suitable for ion mobility separation and/or collision induced decomposition in various different permutations and combinations.

In a mode of operation ions may initially be separated according to their ion mobility as the ions make a first circuit of the closed-loop ion guide. Some ions may be then selected to perform a second circuit of the closed-loop ion guide whilst other ions may be withdrawn from the closed-loop ion guide and may be subjected to further analysis and/or ion detection. Those ions which are directed to pass around the closed-loop ion guide for a second circuit may be separated further according to their ion mobility. Some or all of the ions may then be withdrawn from the closed-loop ion guide for further analysis and/or ion detection. Alternatively, some or all of the ions may be passed through or around the closed-loop ion guide so that ions make three or more circuits of the closed-loop ion guide before the ions are preferably withdrawn for further analysis and/or ion detection.

Embodiments are contemplated wherein the resolution of the closed-loop ion guide acting as an ion mobility separator or ion mobility spectrometer may be further improved by altering certain conditions between circuits of ions around the closed-loop ion guide. For example, the amplitude of the transient DC voltage or potential applied to the electrodes of the closed-loop ion guide in order to urge ions around the closed-loop ion guide may be varied, altered, increased or decreased from one circuit to the next. Similarly, the rate at which the transient DC voltages are applied to the electrodes of the closed-loop ion guide may be varied, altered, increased or decreased from one circuit to the next.

According to an embodiment one or more of the ion guide sections may encompass a potential restoring function.

According to a less preferred embodiment the closed-loop ion guide may include a conventional ion mobility spectrometer or ion mobility separator section. The ion mobility spectrometer or separator may, for example, comprise a drift tube comprising a plurality of guard rings distributed within the drift tube. The guard rings may be interconnected by equivalent valued resistors and connected to a DC voltage source. A linear DC voltage gradient may be generated along the length of the drift tube. The guard rings may not be connected to an AC or RF voltage source.

According to an embodiment the closed-loop ion guide may include an ion mobility spectrometer or ion mobility separator section comprising a number of ring or annular electrodes or a number of plate electrodes. Alternate electrodes forming the ion mobility spectrometer or ion mobility separator section are preferably coupled to opposite phases of an AC or RF voltage supply. The AC or RF voltage supply preferably has a frequency within the range 0.1-10.0 MHz, preferably 0.3-3.0 MHz, further preferably 0.5-2 MHz. The electrodes comprising the ion mobility spectrometer or ion mobility separator section may be interconnected via resistors to a DC voltage supply which in one embodiment may comprise a 400 V supply. The resistors interconnecting electrodes forming the ion mobility spectrometer or ion mobility separator section may be substantially equal in value in which case a linear axial DC voltage gradient may be provided. The DC voltage gradient may be maintained so to urge ions in the required direction around the closed-loop ion guide. The applied AC or RF voltage is preferably superimposed upon the DC voltage and serves to radially confine ions within the ion mobility spectrometer or ion mobility separator section.

According to some of the less preferred embodiments a greater potential difference may be imposed along a section of the closed-loop ion guide which acts to oppose the onward transmission of the ions. According to these embodiments one or more transient DC voltages or one or more transient DC voltage waveforms may need to be applied to the electrodes adjacent to the section of the ion guide which has a relatively large potential difference which opposes the onward transmission of ions in order to propel the ions across the potential difference or restoring potential.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising a closed-loop ion guide comprising:
   a plurality of electrodes,
   an AC or RF voltage supply for applying an AC or RF voltage to the plurality of electrodes, said AC or RF voltage generating a pseudo-potential well which acts to confine ions radially within said closed-loop ion guide, and a DC voltage supply for progressively applying one more transient DC voltages or potentials or DC voltage or potential waveforms to at least some of the electrodes of the ion guide so as to drive or urge ions along or around at least some of the length or ion guiding path of said ion guide.

2. A mass spectrometer as claimed in claim 1, wherein in a mode of operation ions are arranged to make multiple circuits or rotations of or around said closed-loop ion guide.

3. A mass spectrometer as claimed in claim 1, wherein said plurality of electrodes comprise electrodes having apertures through which ions are transmitted in use.

4. A mass spectrometer comprising a closed-loop ion guide comprising:
   a plurality of electrodes;
   an AC or RF voltage supply for applying an AC or RF voltage to the plurality of electrodes, said AC or RF voltage generating a pseudo-potential well which acts to confine ions radially within said closed-loop ion guide; and
   a DC voltage supply arranged to maintain a constant non-zero DC voltage gradient along at least some of the length or ion guiding path of said ion guide.

5. A mass spectrometer comprising a closed-loop ion guide comprising:
   a plurality of electrodes, and
   an AC or RF voltage supply for applying an AC or RF voltage to the plurality of electrodes, said AC or RF voltage generating a pseudo-potential well which acts to confine ions radially within said closed-loop ion guide, wherein one or more portions of said ion guide comprise an ion mobility spectrometer or separator portion, section or stage wherein ions are caused to separate temporally according to their ion mobility in said ion mobility spectrometer or separator portion, section or stage.

6. A mass spectrometer as claimed in claim 1, wherein in use a buffer gas is provided within one or more sections of said ion guide.

7. A mass spectrometer as claimed in claim 1, comprising means for injecting ions into or ejecting ions from said ion guide, wherein said means for injecting or ejecting ions comprises one, two, three or more than three discrete ion guiding channels or ion guiding regions through which ions may be injected into or ejected from said ion guide.

8. A mass spectrometer as claimed in claim 7, wherein said means for injecting or ejecting ions further comprises one or more deflection electrodes, wherein in use one or more voltages are applied to said one or more deflection electrodes in order to direct ions from said one or more ion guiding channels or ion guiding regions into said ion guide or direct ions from said ion guide into said one or more ion guiding channels or ion guiding regions.

9. A mass spectrometer as claimed in claim 1, further comprising a device for maintaining in a mode of operation at least a portion of said ion guide at a pressure selected from the group consisting of: (i) $>1.0\times10^{-3}$ mbar; (ii) $>1.0\times10^{-2}$ mbar; (iii) $>1.0\times10^{-1}$ mbar; (iv) $>1$ mbar; (v) $>10$ mbar; (vi) $>100$ mbar; (vii) $>5.0\times10^{-3}$ mbar; (viii) $>5.0\times10^{-2}$ mbar; (ix) $10^{-4}$-$10^{-3}$ mbar; (x) $10^{-3}$-$10^{-2}$ mbar; and (xi) $10^{-2}$-$10^{-1}$ mbar.

10. A mass spectrometer as claimed in claim 1, further comprising a device for maintaining in a mode of operation at least a length L of said ion guide at a pressure P wherein the product P×L is selected from the group consisting of: (i) $\geq 1.0\times10^{-3}$ mbar cm; (ii) $\geq 1.0\times10^{-2}$ mbar cm; (iii) $\geq 1.0\times10^{-1}$ mbar cm; (iv) $\geq 1$ mbar cm; (v) $\geq 10$ mbar cm; (vi) $\geq 10^{2}$ mbar cm; (vii) $\geq 10^{3}$ mbar cm; (viii) $\geq 10^{4}$ mbar cm; and (ix) $\geq 10^{5}$ mbar cm.

11. A mass spectrometer as claimed in claim 1, further comprising at least one of: (i) one or more mass filters; (ii) one or more further ion guides or ion traps; (iii) a collision, fragmentation or reaction device; and (iv) a mass analyser arranged upstream of or within or downstream of said closed-loop ion guide.

12. A method of mass spectrometry comprising:
   guiding ions through a closed-loop ion guide comprising a plurality of electrodes;
   applying an AC or RF voltage to the plurality of electrodes to generate a pseudo-potential well which acts to confine ions radially within said closed-loop ion guide; and progressively applying one more transient DC voltages or potentials or DC voltage or potential waveforms to at least some of the electrodes of the ion guide so as to drive or urge ions along or around at least some of the length or ion guiding path of said ion guide.

13. A method of mass spectrometry comprising:
   guiding ions through a closed loop ion guide including a plurality of electrodes;
   applying an AC or RF voltage to the plurality of electrodes to generate a pseudo-potential well which acts to confine ions radially within the closed loop ion guide;
   progressively applying one or more transient DC voltages or potentials or DC voltage or potential waveforms to at least some of the electrodes of the ion guide so as to drive or urge ions along or around at least some of the length of the ion guiding path of said ion guide;
   causing said ions to make multiple circuits or rotations around said closed loop ion guide in a mode of operation;
   separating temporally the ions according to their ion mobility in an ion mobility spectrometer or separator portion of the ion guide;
   injecting ions into or ejecting ions from said ion guide by using discrete ion guiding channels through which ions may be injected into or ejected from the ion guide; and
   using deflection electrodes in order to direct ions from or into said ion guiding channels.

14. A method of mass spectrometry comprising:
   guiding ions through a closed-loop ion guide comprising a plurality of electrodes;
   applying an AC or RF voltage to the plurality of electrodes to generate a pseudo-potential well which acts to confine ions radially within said closed-loop ion guide; and
   maintaining a constant non-zero DC voltage gradient along at least some of the length or ion guiding path of said ion guide.

15. A method of mass spectrometry comprising:
   guiding ions through a closed-loop ion guide comprising a plurality of electrodes wherein one or more portions of said ion guide comprise an ion mobility spectrometer or separator portion, section or stage;
applying an AC or RF voltage to the plurality of electrodes to generate a pseudo-potential well which acts to confine ions radially within said closed-loop ion guide; and causing ions to separate temporally according to their ion mobility in said ion mobility spectrometer or separator portion, section or stage.

* * * * *